(12) United States Patent
McClurken et al.

(10) Patent No.: US 6,953,461 B2
(45) Date of Patent: Oct. 11, 2005

(54) FLUID-ASSISTED MEDICAL DEVICES, SYSTEMS AND METHODS

(75) Inventors: Michael E. McClurken, Durham, NH (US); David Lipson, North Andover, MA (US); E. Arnold Oyola, Raymond, NH (US)

(73) Assignee: TissueLink Medical, Inc., Dover, NH (US)

( * ) Notice: Subject to any disclaimer, the term of this patent is extended or adjusted under 35 U.S.C. 154(b) by 100 days.

(21) Appl. No.: 10/147,373

(22) Filed: May 16, 2002

(65) Prior Publication Data

US 2003/0216733 A1 Nov. 20, 2003

(51) Int. Cl.[7] ............................................. A61B 18/18
(52) U.S. Cl. ..................................... 606/51; 606/206
(58) Field of Search ....................... 606/41, 45, 48–52, 606/206, 207; 607/101–105

(56) References Cited

U.S. PATENT DOCUMENTS

| | | | |
|---|---|---|---|
| 1,904 A | 10/1840 | Yates et al. | |
| 2,037 A | 7/1841 | Yates et al. | |
| 2,031,682 A | 2/1936 | Wappler et al. | |
| 3,163,166 A | 12/1964 | Brent et al. | |
| 3,901,241 A | 8/1975 | Allen, Jr. | |

(Continued)

FOREIGN PATENT DOCUMENTS

| | | |
|---|---|---|
| EP | 0895756 | 2/1999 |
| EP | 0 956 826 A2 | 11/1999 |
| JP | 57-117843 | 7/1982 |
| WO | WO 90/03152 | 4/1990 |
| WO | WO 94/26228 | 11/1994 |
| WO | WO 95/05781 | 3/1995 |
| WO | WO 95/09570 | 4/1995 |
| WO | WO 95/17222 | 6/1995 |
| WO | WO 96/34571 | 11/1996 |
| WO | WO 97/05829 | 2/1997 |
| WO | WO 97/16127 | 5/1997 |
| WO | WO 98/14131 | 4/1998 |
| WO | WO 99/03414 | 1/1999 |
| WO | WO 01/28444 A1 | 4/2001 |
| WO | WO 01/66026 A2 | 9/2001 |
| WO | WO 01/66026 * | 9/2001 |
| WO | WO 01/80757 A2 | 11/2001 |
| WO | WO 01/82812 A1 | 11/2001 |
| WO | WO 02/24089 A1 | 3/2002 |
| WO | WO 02/069821 | 9/2002 |
| WO | WO 02/071966 A1 | 9/2002 |
| WO | WO 03/020339 A2 | 3/2003 |
| WO | WO 03/024349 A1 | 3/2003 |
| WO | WO 03/049631 A | 6/2003 |
| WO | WO 03/082134 A1 | 10/2003 |

OTHER PUBLICATIONS

"Surface Energy Calculations"—First Ten Angstroms, Applications Notes—2 pages, dated Sep. 13, 2001.

Primary Examiner—Michael Peffley
(74) Attorney, Agent, or Firm—Merchant & Gould P.C.

(57) ABSTRACT

Surgical devices, systems and methods for treating tissue are provided. An exemplary surgical device comprises a tip portion including first and second jaws each having a tissue grasping surface, at least one of the jaws being movable toward the other jaw. The tissue grasping surface of each jaw has includes an electrically insulative surface. The device also includes first and second electrodes connectable to different terminals of an RF generator to generate electrical current flow therebetween, with each of the electrodes having an electrode surface. One of the electrode surfaces is located on one of the jaws separated from one edge of the tissue grasping surface, and the other of the electrode surfaces is located on one or the other of the jaws separated from the other edge of the tissue grasping surface. The device also includes at least one fluid passage being connectable to a fluid source.

58 Claims, 21 Drawing Sheets

U.S. PATENT DOCUMENTS

| | | | |
|---|---|---|---|
| 4,037,590 A | | 7/1977 | Dohring et al. |
| 4,307,720 A | | 12/1981 | Weber, Jr. |
| 4,326,529 A | | 4/1982 | Doss et al. |
| 4,532,924 A | | 8/1985 | Auth et al. |
| 4,567,890 A | | 2/1986 | Ohta et al. |
| 4,602,628 A | | 7/1986 | Allen, Jr. |
| 4,920,982 A | | 5/1990 | Goldstein |
| 4,985,030 A | | 1/1991 | Melzer et al. |
| 5,035,696 A | | 7/1991 | Rydell |
| 5,122,138 A | | 6/1992 | Manwaring |
| 5,151,102 A | | 9/1992 | Kamiyama et al. |
| 5,156,613 A | | 10/1992 | Sawyer |
| 5,167,659 A | | 12/1992 | Ohtomo et al. |
| 5,190,541 A | | 3/1993 | Abele et al. |
| 5,217,460 A | * | 6/1993 | Knoepfler ............... 606/52 |
| 5,242,442 A | | 9/1993 | Hirschfeld |
| 5,269,781 A | | 12/1993 | Hewell, III |
| 5,300,087 A | | 4/1994 | Knoepfler |
| 5,318,589 A | | 6/1994 | Lichtman |
| 5,334,193 A | | 8/1994 | Nardella |
| 5,342,357 A | | 8/1994 | Nardella |
| 5,342,359 A | | 8/1994 | Rydell |
| 5,364,394 A | | 11/1994 | Mehl |
| 5,395,312 A | | 3/1995 | Desai |
| 5,395,363 A | | 3/1995 | Billings et al. |
| 5,401,272 A | | 3/1995 | Perkins |
| 5,403,311 A | | 4/1995 | Abele et al. |
| 5,403,312 A | | 4/1995 | Yates et al. |
| 5,405,344 A | | 4/1995 | Williamson et al. |
| 5,405,376 A | | 4/1995 | Mulier et al. |
| 5,431,649 A | | 7/1995 | Mulier et al. |
| 5,433,708 A | | 7/1995 | Nichols et al. |
| 5,437,664 A | | 8/1995 | Cohen et al. |
| 5,456,682 A | | 10/1995 | Edwards et al. |
| 5,456,684 A | * | 10/1995 | Schmidt et al. ............ 606/41 |
| 5,458,596 A | | 10/1995 | Lax et al. |
| 5,458,597 A | | 10/1995 | Edwards et al. |
| 5,458,598 A | | 10/1995 | Feinberg et al. |
| 5,472,441 A | | 12/1995 | Edwards et al. |
| 5,542,928 A | | 8/1996 | Evans et al. |
| 5,569,242 A | | 10/1996 | Lax et al. |
| 5,584,872 A | | 12/1996 | LaFontaine et al. |
| 5,599,350 A | | 2/1997 | Schulze et al. |
| 5,605,539 A | | 2/1997 | Bueina et al. |
| 5,609,151 A | | 3/1997 | Mulier et al. |
| 5,637,110 A | | 6/1997 | Pennybacker et al. |
| 5,643,197 A | | 7/1997 | Brucker et al. |
| 5,647,871 A | | 7/1997 | Levine et al. |
| 5,653,692 A | | 8/1997 | Masterson et al. |
| 5,676,693 A | | 10/1997 | LaFontaine |
| 5,688,270 A | | 11/1997 | Yates et al. |
| 5,697,281 A | | 12/1997 | Eggers et al. |
| 5,697,536 A | | 12/1997 | Eggers et al. |
| 5,697,909 A | | 12/1997 | Eggers et al. |
| 5,697,927 A | | 12/1997 | Imran et al. |
| 5,709,680 A | | 1/1998 | Yates et al. |
| 5,718,701 A | | 2/1998 | Shai et al. |
| 5,725,524 A | | 3/1998 | Mulier et al. |
| 5,746,739 A | | 5/1998 | Sutter |
| 5,749,869 A | | 5/1998 | Lindenmeier et al. |
| 5,755,717 A | | 5/1998 | Yates et al. |
| 5,800,482 A | | 9/1998 | Pomeranz et al. |
| 5,807,393 A | | 9/1998 | Williamson, IV et al. |
| 5,807,395 A | | 9/1998 | Mulier et al. |
| 5,810,811 A | * | 9/1998 | Yates et al. ............... 606/50 |
| 5,817,093 A | | 10/1998 | Williamson, IV et al. |
| 5,827,271 A | | 10/1998 | Buysse et al. |
| 5,833,703 A | | 11/1998 | Manushakian |
| 5,868,739 A | | 2/1999 | Lindenmeier et al. |
| 5,876,398 A | | 3/1999 | Mulier et al. |
| 5,888,198 A | | 3/1999 | Eggers et al. |
| 5,891,095 A | | 4/1999 | Eggers et al. |
| 5,891,141 A | | 4/1999 | Rydell |
| 5,895,417 A | | 4/1999 | Pomeranz et al. |
| 5,897,553 A | | 4/1999 | Mulier et al. |
| 5,902,328 A | | 5/1999 | LaFontaine et al. |
| 5,906,613 A | | 5/1999 | Mulier et al. |
| 5,913,854 A | | 6/1999 | Maguire et al. |
| 5,951,549 A | | 9/1999 | Richardson et al. |
| 5,964,755 A | | 10/1999 | Edwards |
| 5,976,128 A | | 11/1999 | Schilling et al. |
| 5,980,516 A | | 11/1999 | Mulier et al. |
| 5,992,418 A | | 11/1999 | de la Rama et al. |
| 6,016,809 A | | 1/2000 | Mulier et al. |
| 6,024,733 A | | 2/2000 | Eggers et al. |
| 6,059,781 A | | 5/2000 | Yamanashi et al. |
| 6,063,081 A | | 5/2000 | Mulier et al. |
| 6,074,389 A | * | 6/2000 | Levine et al. ............. 606/45 |
| 6,086,586 A | | 7/2000 | Hooven |
| 6,096,037 A | * | 8/2000 | Mulier et al. ............. 606/49 |
| 6,113,596 A | | 9/2000 | Hooven et al. |
| 6,165,175 A | | 12/2000 | Wampler et al. |
| 6,174,309 B1 | | 1/2001 | Wrublewski et al. |
| 6,210,411 B1 | | 4/2001 | Hofmann et al. |
| 6,238,393 B1 | | 5/2001 | Mulier et al. |
| 6,302,903 B1 | | 10/2001 | Mulier et al. |
| 6,312,430 B1 | | 11/2001 | Wilson et al. |
| 6,315,777 B1 | | 11/2001 | Comben |
| 6,327,505 B1 | | 12/2001 | Medhkour et al. |
| 6,328,736 B1 | | 12/2001 | Mulier et al. |
| 6,358,248 B1 | | 3/2002 | Mulier et al. |
| 6,409,722 B1 | | 6/2002 | Hoey et al. |
| 6,451,017 B1 | | 9/2002 | Moutafis et al. |
| 6,458,130 B1 | | 10/2002 | Frazier et al. |
| 6,468,275 B1 | | 10/2002 | Wampler et al. |
| 6,485,490 B2 | | 11/2002 | Wampler et al. |
| 6,488,680 B1 | | 12/2002 | Francischelli et al. |
| 6,493,589 B1 | | 12/2002 | Medhkour et al. |
| 6,558,385 B1 | | 5/2003 | McClurken et al. |
| 6,676,660 B2 | | 1/2004 | Wampler et al. |
| 2001/0023356 A1 | | 9/2001 | Medhkour et al. |
| 2001/0032002 A1 | | 10/2001 | McClurken et al. |
| 2001/0039419 A1 | | 11/2001 | Francischelli et al. |
| 2002/0049439 A1 | | 4/2002 | Mulier et al. |
| 2002/0058933 A1 | | 5/2002 | Christopherson et al. |
| 2002/0058935 A1 | | 5/2002 | Hoey et al. |
| 2002/0062123 A1 | * | 5/2002 | McClurken et al. .......... 606/34 |
| 2002/0128650 A1 | | 9/2002 | McClurken |
| 2003/0114850 A1 | | 6/2003 | McClurken et al. |

* cited by examiner

FLUID-ASSISTED MEDICAL DEVICES, SYSTEMS AND METHODS

FIELD

This invention relates generally to the field of medical devices, systems and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

The application of heat to tissue, typically from a flame heated metal object, has been used for centuries to cauterize bleeding wounds. In cauterization, the essential mechanism behind tissue treatment involves raising the temperature of the bleeding tissue by conductive heat transfer from the heated metal object. In order to arrest bleeding from the tissue's severed blood vessels, the tissue is heated adequately to shrink certain tissue proteins, such as collagen, thus closing the blood vessels and ultimately leading to blood vessel thrombosis.

Apart from shrinkage, the application of compressive force from a heated metal object to a blood vessel may also result in collagen welding, such as for the permanent joining together of opposite walls of a blood vessel, thus providing another mechanism of hemostasis in addition to simple shrinkage of collagen.

With the aid of electricity, cauterization spurred the development of electrocautery devices to treat bleeding. While electrocautery devices still involve the use of a heated metal object, the electrocautery device is heated via electrical energy converted to heat in the metal object as opposed to heating the metal with a direct flame.

More recently, coagulation may be accomplished by radio frequency ("RF") electrosurgical devices where electrical energy is converted to heat in the tissue rather than in the device. Heating of the tissue is often performed by means of resistance heating. In other words, increasing the temperature of the tissue as a result of electric current flow through the tissue which is resisted by the tissue. Electrical energy is converted into thermal energy (i.e. heat) via accelerated movement of ions as a function of the tissue's electrical resistance and current flow.

Hemostasis of the above sort is not without its drawbacks. Current dry tip RF electrosurgical devices can cause the temperature of tissue being treated to rise significantly higher than 100° C., thus exceeding the boiling temperature of inter-cellular water and resulting in tissue desiccation, tissue sticking to the electrodes, tissue perforation, char formation and smoke generation. Peak tissue temperatures at a targeted tissue treatment site can be as high as 320° C. as a result of RF treatment, and such high temperatures can be transmitted to adjacent untargeted tissue via conduction. Undesirable results of such transmission to untargeted adjacent tissue include unintended thermal damage to the untargeted tissue.

According to U.S. Pat. No. 6,086,586 to Hooven entitled "Bipolar Tissue Grasping Apparatus and Tissue Welding Method", currently-available bipolar grasping instruments for electro-coagulation of tissue, or "tissue welding," generally use only two electrodes of opposite polarity, one of which is located on each of the opposite jaws of the grasper.

As illustrated in Hooven's FIG. 1, in use, tissue is held between a pair of grasper jaws (shown in cross-section) having first and second electrodes (Electrode 1 and Electrode 2) of opposite polarity. Bipolar current flows between the two electrodes along the illustrated current flow lines, with tissue coagulating first at the edges of the jaws. Then, as the tissue dries out and the impedance increases, the current flows through the moister tissue and the coagulation spreads both inward toward the center of the jaws and outward from the jaw edges.

The Hooven patent goes on to recite that "[t]hermal damage to adjacent structures can occur due to this spread of thermal energy outside the jaws of the instrument. Because of the spread of thermal energy outside the jaws of the instrument, it is difficult to coagulate long sections of tissue, such as bowel, lung, or larger blood vessels, without significant lateral thermal spread. Over-coagulation frequently occurs, resulting in tissue sticking to the jaws of the instrument. When the jaws of the instrument are opened, if the tissue sticking is severe, the tissue can be pulled apart, thus adversely affecting hemostasis."

As part of the summary of the invention, the Hooven patent recites "a bipolar electrosurgical instrument having a pair of relatively moveable jaws, each of which includes a tissue contacting surface. The tissue contacting surfaces of the jaws are in face-to-face relation with one another, and adjacent each of the tissue contacting surfaces are first and second spaced-apart electrodes that are adapted for connection to the opposite terminals of a bipolar RF generator so as to generate a current flow therebetween." Furthermore, the Hooven patent recites that, "[b]ecause each jaw is a bipolar electrode, multiple local current pathways, high current densities, and lower impedances are achieved. Indeed, the maximum current density is between the two insulated jaw surfaces, while a relatively lower current density exists at the electrode surfaces."

However, the invention of the Hooven patent encounters certain difficulties. Due to tissue irregularities, the surface of the tissue to be treated may be uneven or undulated with peaks and valleys. Consequently, the area of electrical coupling of the tissue to the electrode surfaces can be limited to the isolated peaks in the tissue surface. In this situation, upon the application of RF power to tissue, the electrical coupling of only the tissue peaks to the electrode surfaces may result in corresponding increase in current density through the electrically coupled peaks which has the ability to desiccate and char the tissue at these isolated locations. Hooven does not address or provide for this situation.

Another difficulty encountered with the Hooven invention is that it does not address or provide for a decreasing electrical coupling between the tissue and electrode surfaces upon tissue shrinkage and/or desiccation during treatment. As tissue shrinks and/or desiccates during treatment, the tissue surfaces may loose contact with the electrode surfaces which, similar to above, decreases the area of electrical coupling therebetween and correspondingly increases the current density and associated heat at the locations which remain electrically coupled. This difficulty is further exacerbated if the tissue is undulated as described above.

Another difficulty encountered with the Hooven invention is that it does not address or provide for dissipating heat from the insulating members. Hooven does not address or provide how heat which may be conducted into the insulating members from the tissue between the two insulated surfaces is subsequently removed from the insulating members.

In light of the above, it is an object of the invention to provide devices, systems and methods which overcome the limitations of the art.

SUMMARY OF THE INVENTION

The present invention provides devices, systems and methods that inhibit, and more preferably minimize or prevent, tissue necrosis outside a targeted tissue treatment site during a medical procedure. The invention is particularly useful during surgical procedures upon tissues of a human body, where it is desirable to coagulate and shrink tissue, to occlude lumens of blood vessels (e.g. arteries, veins), airways (e.g. bronchi, bronchioles), bile ducts and lymphatic ducts.

According to the present invention, electrosurgical devices, systems and methods are provided in which the electrical current paths, associated electrical resistance heating and ensuing thermal conduction heating are substantially limited to tissue within the jaws of the device, so as to inhibit, and preferably prevent, tissue damage outside the jaws due to thermal effects. More preferably, the electrical current paths, as well as current density, are concentrated within the confines and borders of two electrically insulated surfaces of the jaws and, even more preferably, within the medial portions of the electrically insulated surfaces.

According to the present invention, electrosurgical devices, systems and methods are provided in which the maximum current density and heating of tissue (by both electrical resistance heating and thermal conduction heating) occurs apart or removed from the electrodes and preferably between the two electrically insulated surfaces. More preferably, the electrodes are configured such that the portion of the electrode surfaces closest to the two electrically insulated surfaces is remotely located and separated from the electrically insulated surfaces.

According to the present invention, electrosurgical devices, systems and methods are provided in which the electrical coupling between tissue and the electrodes is enhanced, so as to inhibit tissue damage outside the electrically insulated surfaces, particularly to tissue nearest the electrodes. Tissue damage can be manifest in many ways, depending on the tissue temperature encountered, ranging from coagulation necrosis at temperatures from 50 to 100° C., to sticking at temperatures above 120° C., to charring, arcing and smoke formation at temperatures exceeding 200° C.

According to the present invention, preferably the enhanced electrical coupling is provided by an electrically conductive fluid which couples between the tissue surface and the electrodes and increases the uniformity of the electrical coupling therebetween. In addition to inhibiting tissue damage as outlined above, this enhancement is particularly useful to counter poor electrical coupling associated with prior art dry devices, uneven and undulated tissue, shrinkage of treated tissue, desiccation of treated tissue and motion of the jaws while grasping tissue.

According to the present invention, electrosurgical devices, systems and methods are provided in which a portion of the electrical current, upon exiting from between the two electrically insulated surfaces, flows at least partially through the electrically conductive fluid, rather than through the tissue outside the electrically insulated surfaces, before reaching the counter electrode. According to the present invention, this will inhibit tissue damage outside the electrically insulated surfaces given the decrease in electrical current through the tissue and associated decrease in power in the tissue will correspondingly reduce the amount of resistance and conduction heating of the tissue.

According to the present invention, electrosurgical devices, systems and methods are provided and configured to provide a diversion and preferably divert at least a portion of the electrical current, upon exiting from between the two electrically insulated surfaces, at least partially through the conductive fluid before reaching the counter electrode. Preferably at least a portion of the electrically conductive fluid coupling the electrodes and the tissue outside the electrically insulated surfaces electrical couples tissue adjacent the electrically insulated surfaces. Also, preferably, at least a portion of the electrically conductive fluid coupling the electrodes and the tissue adjacent the electrically insulated surfaces electrical couples the tissue and the electrodes at the shortest distance there between.

Preferably the electrosurgical devices, systems and methods are configured such that the electrical current exiting from between the two electrically insulated surfaces will be more apt to be concentrated and flow at least partially through the electrically conductive fluid, rather than through the tissue outside the electrically insulated surfaces, to the counter electrode.

Preferably the electrically conductive fluid is provided in a configuration to present an electrical resistance to the electrical current exiting from between the two electrically insulated surfaces which is less than the electrical resistance encountered in tissue outside the electrically insulated surfaces. Preferably the electrically conductive fluid has an electrical resistivity less than the electrical resistivity of the tissue through which electrical current would flow in the absence of the electrically conductive fluid prior to treatment with the device.

According to the present invention, the source electrode side relative to the tissue grasping surfaces is configured similar to the counter electrode side. As electrical current flows from the source electrode and enters between the tissue grasping surfaces it will also seek a path to the counter electrode comprising the least electrical resistance. Consequently, in addition to the above, the device is also configured to provide a diversion for and preferably divert at least a portion of the electrical current, upon leaving the source electrode, at least partially through the conductive fluid before entering between the grasping surfaces.

Preferably the electrically conductive fluid is provided to tissue by means of the electrosurgical device. Also preferably, the electrically conductive fluid comprises a saline solution. Furthermore, in certain embodiments, the saline solution may comprise physiologic saline or hypertonic saline.

According to the present invention, electrosurgical devices, systems and methods are provided in which removal of heat from and cooling of the tissue outside the electrically insulated surfaces is enhanced, so as to inhibit tissue damage outside the electrically insulated surfaces. Preferably, the enhanced cooling is provided by a fluid, particularly the electrically conductive fluid. More particularly, in the event a portion of the electrical current exiting from between the two electrically insulated surfaces flows through tissue outside the electrically insulated surfaces, thus heating the tissue outside the electrically insulated surfaces by resistance and conduction heating, the conductive fluid function as a heat sink to absorb and remove heat from the tissue and cool the tissue. Furthermore, it is an object of the present invention that the conductive fluid lubricates the tissue/electrode interface and the tissue/electrically insulated surface interface as to inhibit sticking thereto.

According to the present invention, electrosurgical devices, systems and methods are provided which are configured to remove heat from and cool the jaws, particularly the electrically insulated surfaces of the jaws, and more particularly the medial portion of the insulated surfaces. In some embodiments, the electrically insulated surfaces of the jaws comprise or are supported by a material with a high thermal conductivity. In other embodiments, heat is removed from the jaws by the electrically conductive fluid.

According to the present invention, electrosurgical devices, systems and methods are provided for medical procedures, which preferably utilize radio frequency ("RF") power and electrically conductive fluid during the treatment of tissue. Preferably, the temperature of the tissue, particularly outside a targeted tissue treatment site (e.g. outside the electrically insulated surfaces of the jaws), may be altered and at least partially controlled (e.g. maintained within a targeted temperature range or at a targeted tissue temperature) by adjusting parameters (e.g. the fluid flow rate of the electrically conductive fluid) that affect the temperature of the tissue.

According to the present invention, using a fluid in the above manner inhibits, and preferably minimizes or prevents tissue damage (e.g. necrosis), and such undesirable effects as tissue sticking to electrodes, smoke generation, char formation and desiccation, to tissue outside a targeted tissue treatment site.

According to the present invention, a tissue grasping device is provided comprising a tip portion including a first jaw and a second jaw with at least one of the jaws being movable toward the other jaw. The first jaw includes a first tissue grasping surface and the second jaw includes a second tissue grasping surface. The tissue grasping surface of each jaw has a length defined by proximal and distal ends, a width defined by edges and further comprises an electrically insulative surface. The device further comprises first and second electrodes being connectable to different terminals of a radio frequency generator to generate electrical current flow therebetween, with the first electrode having a first electrode surface and the second electrode having a second electrode surface. One of the first and second electrode surfaces is located on one or the other of the jaws separated from one edge of the tissue grasping surface and the other of the electrode surfaces is located on one or the other of the jaws separated from the other edge of the tissue grasping surface. The device also includes at least one fluid passage being connectable to a fluid source.

According to the present invention, a device is provided with a tip portion configured to provide radio frequency power from a radio frequency generator with a fluid from a fluid source to tissue, with the fluid provided to the tissue at a tissue surface and the radio frequency power provided to the tissue below the tissue surface.

According to another aspect of the present invention, a device is provided with a tip portion configured to provide radio frequency power to tissue at least partially through a fluid coupling located on a surface of the tissue, with the fluid coupling comprising an electrically conductive fluid provided from a fluid source and the electrically conductive fluid provided from the tip portion with the radio frequency power.

According to another aspect of the invention, a device is provided that is configured to receive radio frequency power from a radio frequency generator at a power level and an electrically conductive fluid from a fluid source at a fluid flow rate, and deliver the electrically conductive fluid to tissue at a tissue surface and the radio frequency power to the tissue below the tissue surface.

According to yet another aspect to the invention, a device is provided that is configured to receive radio frequency power from a radio frequency generator at a power level and an electrically conductive fluid from a fluid source at a fluid flow rate, and deliver the electrically conductive fluid to tissue at a tissue surface and the radio frequency power to the tissue below the tissue surface at least partially through a fluid coupling comprising the electrically conductive fluid.

In certain embodiments, the tip portion further comprises at least one fluid outlet in fluid communication with a fluid passage configured to provide a fluid from a fluid source to tissue. Preferably, the at least one fluid outlet in fluid communication with the fluid passage further comprises a first fluid outlet and a second fluid outlet with the first fluid outlet being located on the same jaw as a first electrode and the second fluid outlet being located on the same jaw as a second electrode. Preferably, the first fluid outlet and the second fluid outlet are configured to receive the fluid from the fluid source and provide the fluid to tissue located outside of tissue grasping surfaces.

In one embodiment, a first fluid outlet and a second fluid outlet are configured to receive a fluid from a fluid source and provide the fluid to tissue located outside of and adjacent tissue grasping surfaces.

In another embodiment, a first fluid outlet and a second fluid outlet are configured to receive a fluid from a fluid source and provide the fluid to tissue located outside of and separated from tissue grasping surfaces.

In another embodiment, a first fluid outlet is configured to provide a fluid to tissue located adjacent a first electrode surface, and a second fluid outlet is configured to provide a fluid to tissue located adjacent a second electrode surface.

In another embodiment, a first fluid outlet is configured to provide a fluid between a first electrode surface and tissue, and a second fluid outlet is configured to provide a fluid between a second electrode surface and tissue.

In another embodiment, a first fluid outlet is configured to provide a fluid between a first electrode surface and one edge of one or the other of two tissue grasping surfaces, and a second fluid outlet is configured to provide a fluid between a second electrode surface and the other edge of one or the other of the tissue grasping surfaces.

In another embodiment, a first fluid outlet is configured to provide a fluid to the first electrode surface, and a second fluid outlet is configured to provide a fluid to a second electrode surface.

In another embodiment, a first fluid outlet is configured to provide a fluid to a first portion of one or the other of two jaws outside a tissue grasping surface, and a second fluid outlet is configured to provide a fluid to a second portion of one or the other of the jaws outside a tissue grasping surface.

In one embodiment, each of two first and second electrode surfaces is separated from a tissue grasping surface of a jaw to which it is located by a gap. In another embodiment, at least a portion of each gap separating each of the first and second electrode surfaces from the tissue grasping surface of the jaw to which it is located is configured to receive a fluid from a fluid source. In another embodiment, the fluid received by each of the gaps is configured to provide a fluid coupling which provides cooling and removing heat from tissue located outside the tissue grasping surfaces. In yet another embodiment, the fluid comprises an electrically conductive fluid, and the fluid received by each of the gaps is configured to provide a fluid coupling which enhances the electrical connection of the first and second electrode surfaces and tissue located outside the tissue grasping surfaces. Furthermore, in yet another embodiment, at least a portion of the electrical current flow between the first and second electrode surfaces may be caused to flow at least partially through at least one fluid coupling as opposed to tissue located outside the tissue grasping surfaces, whereby the amount of current flow through tissue located outside the tissue grasping surfaces may be correspondingly reduced. In one embodiment, the tissue grasping surface of each jaw has a length, and each gap further comprises an elongated gap separating each of the first and second electrode surfaces from the tissue grasping surface of the jaw to which it is located along the length of the tissue grasping surface. In another embodiment, at least a portion of each elongated gap separating each of the first and second electrode surfaces from the tissue grasping surface of the jaw to which it is located is configured to receive a fluid from the fluid source and provide a fluid flow channel for the fluid along the length of the tissue grasping surface.

In yet another embodiment, at least one jaw comprises at least one stand-off configured to keep tissue from physically contacting at least one of a first electrode surface and a second electrode surface. In various embodiments, the stand-off preferably comprises a coil wrapped around at least a portion of one of the first and second electrode surface, a material porous to a fluid provided from a fluid source there through with the material overlying at least a portion of one of the first and second electrode surface, or a foam material overlying at least a portion of one of the first and second electrode surface. In other embodiments, the stand-off comprises a polymer or ceramic material.

In other embodiments, at least one jaw comprises at least one obstruction configured to inhibit a fluid shunt from forming between the first electrode and the second electrode. In various embodiments, the obstruction comprises a tissue grasping surface of a jaw, a distal end portion of a jaw, a proximal end portion of a jaw or a backside portion of a jaw, such as a protrusion or recess which provides a drip edge.

In other embodiments, a tissue treatment indicator is provided which provides an output related to a level of treatment of tissue. In certain embodiments, the tissue treatment indicator comprises a bulb or a thermochromic device wired in parallel with an electrode.

According to another aspect of the invention, a tissue grasping device is provided comprising a tip portion including a first jaw and a second jaw with at least one of the jaws being movable toward the other jaw. Each jaw includes a left-side portion, a right-side portion and a tissue grasping surface with the tissue grasping surface of each jaw further comprising an electrically insulative surface. The device further comprises first and second electrodes being connectable to different terminals of a radio frequency generator to generate electrical current flow therebetween with the first electrode having a first electrode surface and the second electrode having a second electrode surface. One of the first and second electrodes is located on one or the other of the jaws on the left-side portion of the jaw and the other of the electrodes is located on one or the other of the jaws on the right-side portion of the jaw. Each of the first and second electrode surfaces is separated from the tissue grasping surface of the jaw on which it is located. The device also includes at least one fluid passage being connectable to a fluid source.

According to another aspect of the invention, a tissue grasping device is provided comprising a tip portion including a first jaw and a second jaw with at least one of the jaws being movable toward the other jaw. Each jaw includes a tissue grasping surface with the tissue grasping surface of each jaw further comprising an electrically insulative surface. A portion of each tissue grasping surface is located on each side of a center plane. The center plane is orientated longitudinal and to the tissue grasping surface. The device further comprises first and second electrodes being connectable to different terminals of a radio frequency generator to generate electrical current flow therebetween with the first electrode having a first electrode surface and the second electrode having a second electrode surface. One of the first and second electrodes is located on one or the other of the jaws on one side of the center plane and the other of the electrodes is located on one or the other of the jaws on the other side of the center plane. Each of the first and second electrode surfaces is separated from the tissue grasping surface of the jaw to which it is located. The device also includes at least one fluid passage being connectable to a fluid source.

According to another aspect of the invention, a tissue grasping device is provided comprising a tip portion including a first jaw and a second jaw with at least one of the jaws being movable toward the other jaw. Each jaw includes a tissue grasping surface with the tissue grasping surface of each jaw further comprising an electrically insulative surface. A portion of each tissue grasping surface is located on two opposing sides of a cutting mechanism, the cutting mechanism comprising a blade. The device further comprises first and second electrodes being connectable to different terminals of a radio frequency generator to generate electrical current flow therebetween with the first electrode having a first electrode surface and the second electrode having a second electrode surface. One of the first and second electrodes is located on one or the other of the jaws on one side of the cutting mechanism and the other of the electrodes is located on one or the other of the jaws on the other side of the cutting mechanism. Each of the first and second electrode surfaces is separated from the tissue grasping surface of the jaw to which it is located. The device also includes at least one fluid passage being connectable to a fluid source.

According to another aspect of the invention, a tissue grasping device is provided comprising a tip portion including a first jaw and a second jaw with at least one of the jaws being movable toward the other jaw. Each jaw includes a tissue grasping surface with the tissue grasping surface of each jaw further comprising an electrically insulative surface. The device further comprises at least two spaced-apart electrode surfaces separated from the tissue grasping surface of each jaw, with the two electrode surfaces on the first jaw in direct opposed relation with the two electrode surfaces on the second jaw, the opposing electrode surfaces being of like polarity and the electrode surfaces of each jaw being connectable to a power source for providing electrical current flow therebetween. The device also includes at least one fluid passage being connectable to a fluid source.

According to another aspect of the invention, a method of treating tissue is provided comprising providing tissue; providing electrical current; providing a fluid; providing a first tissue grasping surface and a second tissue grasping surface; grasping a first portion of tissue with the first portion of tissue located between the tissue grasping surfaces; providing the fluid to a second portion of tissue with the second portion of tissue located outside the tissue grasping surfaces; providing the electric current to the tissue; and directing the electric current in the first portion of tissue to flow across the tissue grasping surfaces. In certain embodiments, the method further comprises the step of cooling the second portion of tissue with the fluid and/or cooling the first portion of tissue with the fluid. Furthermore, in certain embodiments, the step of providing a fluid further comprises providing an electrically conductive fluid, and the method includes the additional step of reducing the electrical current in the second portion of tissue with the fluid.

According to another aspect of the invention, a method of treating tissue is provided comprising providing tissue; providing electrical current; providing a fluid; providing a first tissue grasping surface and a second tissue grasping surface; grasping a first portion of tissue, the first portion of tissue located between the tissue grasping surfaces; providing the fluid to a second portion of tissue, the second portion of tissue located outside the tissue grasping surfaces; providing the electric current to the tissue; and directing the electric current in the first portion of tissue to flow substantially parallel to the tissue grasping surfaces. In certain embodiments, the method further comprises the step of cooling the second portion of tissue with the fluid and/or cooling the first portion of tissue with the fluid. Furthermore, in certain embodiments, the step of providing a fluid further comprises providing an electrically conductive fluid, and the method includes the additional step of reducing the electrical current in the second portion of tissue with the fluid.

According to another aspect of the present invention, a tissue grasping device is provided comprising a tip portion including a first jaw and a second jaw with at least one of the jaws being movable toward the other jaw. Each jaw includes a tissue grasping surface with the tissue grasping surface of each jaw further comprising an electrically insulative surface. The device further comprises at least two electrodes separated by the tissue grasping surfaces and located between the two electrodes with the two electrodes being connectable to different terminals of a radio frequency generator to generate electrical current flow therebetween. The device also includes at least one fluid passage being connectable to a fluid source.

DETAILED DESCRIPTION

Figure 1:
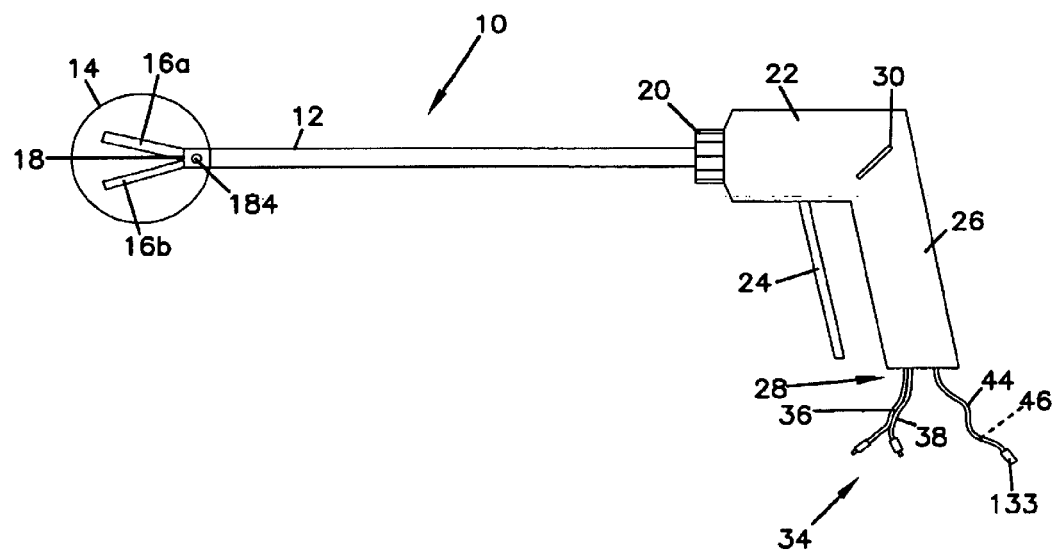
FIG. 1 is a side view of an exemplary device according to the present invention.
Figure 2:
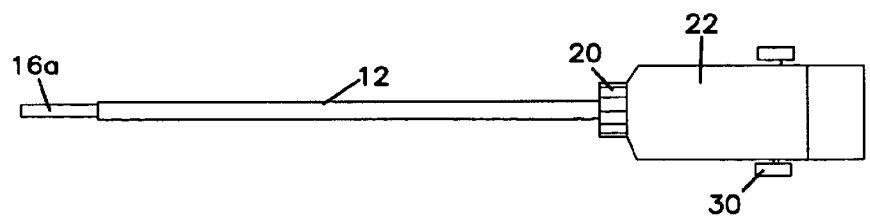
FIG. 2 is a top view of the device of FIG. 1.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive. Also, from the specification, it should be clear that any use of the terms "distal" and "proximal" are made in reference to the user of the device, and not the patient.

An exemplary electrosurgical device according to the present invention will now be described in detail. The electrosurgical device may be used with the system of the invention to be described herein. However, it should be understood that the description of the combination is for purposes of illustrating the system of the invention only. Consequently, it should be understood that the electrosurgical device of the present invention can be used alone, or in conjunction with, the system of the invention. Conversely, it should be equally understood that the system of the present invention can be used with a wide variety of devices.

An exemplary electrosurgical device of the present invention, which may be used in conjunction with one or more aspects of the system of the present invention, is shown at reference character 10 in FIG. 1. FIG. 1 shows a side view of device 10, which is designed and configured to manipulate (e.g. grasp, coagulate and cut) tissue. Device 10 preferably comprises a tissue grasper, particularly forceps and more particularly endoscopic forceps as shown. When device 10 comprises endoscopic forceps, preferably device 10 is configured to extend through a working channel of a trocar cannula.

As shown in FIG. 1, device 10 preferably includes an intermediate portion, comprising a hollow shaft 12, and a tip portion 14. As shown, tip portion 14 preferably comprises two directly opposing, cooperating, relatively moveable jaws 16a, 16b connected and located adjacent the distal end 18 of the shaft 12.

Also as shown in FIG. 1, device 10 also preferably includes a collar 20 for rotating the entire shaft 12 and connecting a proximal handle 22 to the proximal end of the shaft 12 and an actuation lever 24 (preferably comprising a first-class lever) which when squeezed towards the pistol or hand grip portion 26 of the handle 22 in the direction of arrow 28 will close the opposing jaws 16a, 16b in a manner known in the art.

Figure 9:
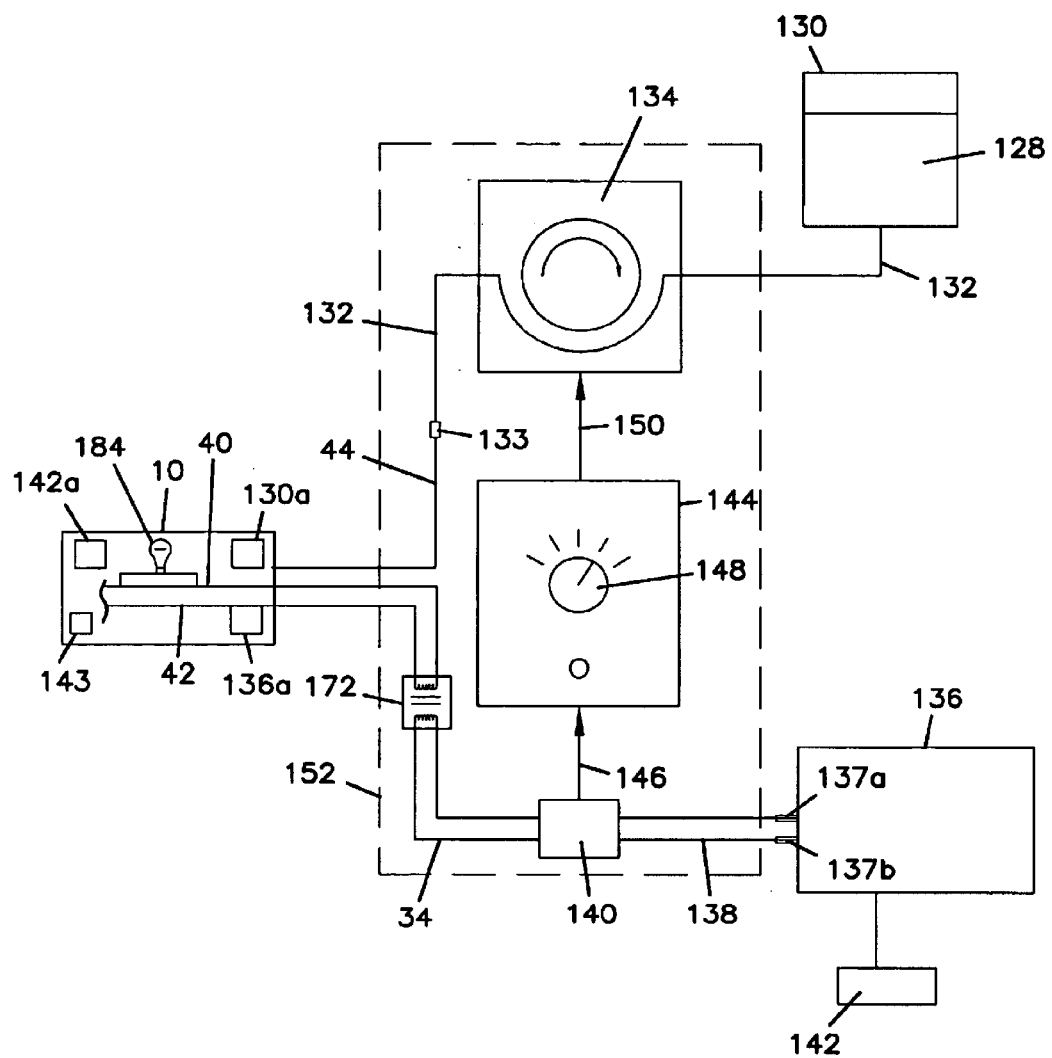
FIG. 9 is an exemplary block diagram showing one embodiment of a system of the invention with the device of FIG. 1.

Continuing with FIG. 1, device 10 also preferably includes a pair of opposing paddles 30 to activate a built-in cutting mechanism 32 (shown in FIG. 5); a cable 34 extending from the butt of the grip portion 26 of handle 22 comprising two insulated wires 36, 38 containing wire conductors 40, 42 (shown in FIGS. 3 and 4) connected and configured to deliver energy (e.g. RF power) to jaws 16a, 16b, preferably through the shaft 12 and handle 22, and connectable to a source of energy (e.g. via plug connectors to plug clip receptacles 137a, 137b of the opposite terminals of a bipolar electrical generator 136 as shown in FIG. 9); and a input fluid line 44 comprising a passage 46 (e.g. lumen) extending from the butt of the grip portion 26 of handle 22 that is connected and configured to deliver fluid 128 (also shown in FIG. 9) via dividing branches to jaws 16a, 16b, also preferably through the shaft 12 and handle 22, and connectable to a fluid source 130 (e.g. saline IV bag shown in FIG. 9).

Figure 3:
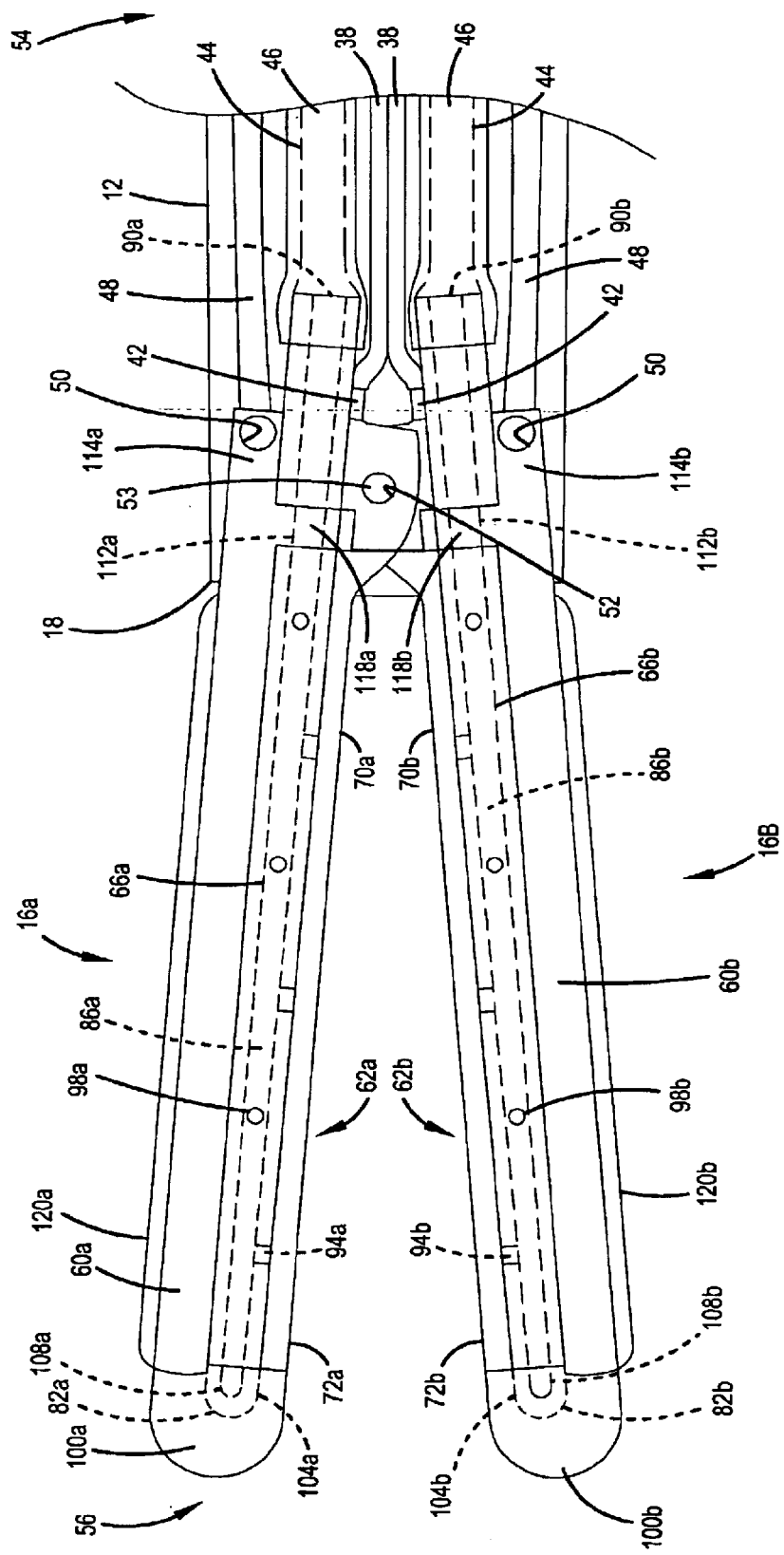
FIG. 3 is a close-up first side view of the tip portion of the device of FIG. 1.
Figure 4:
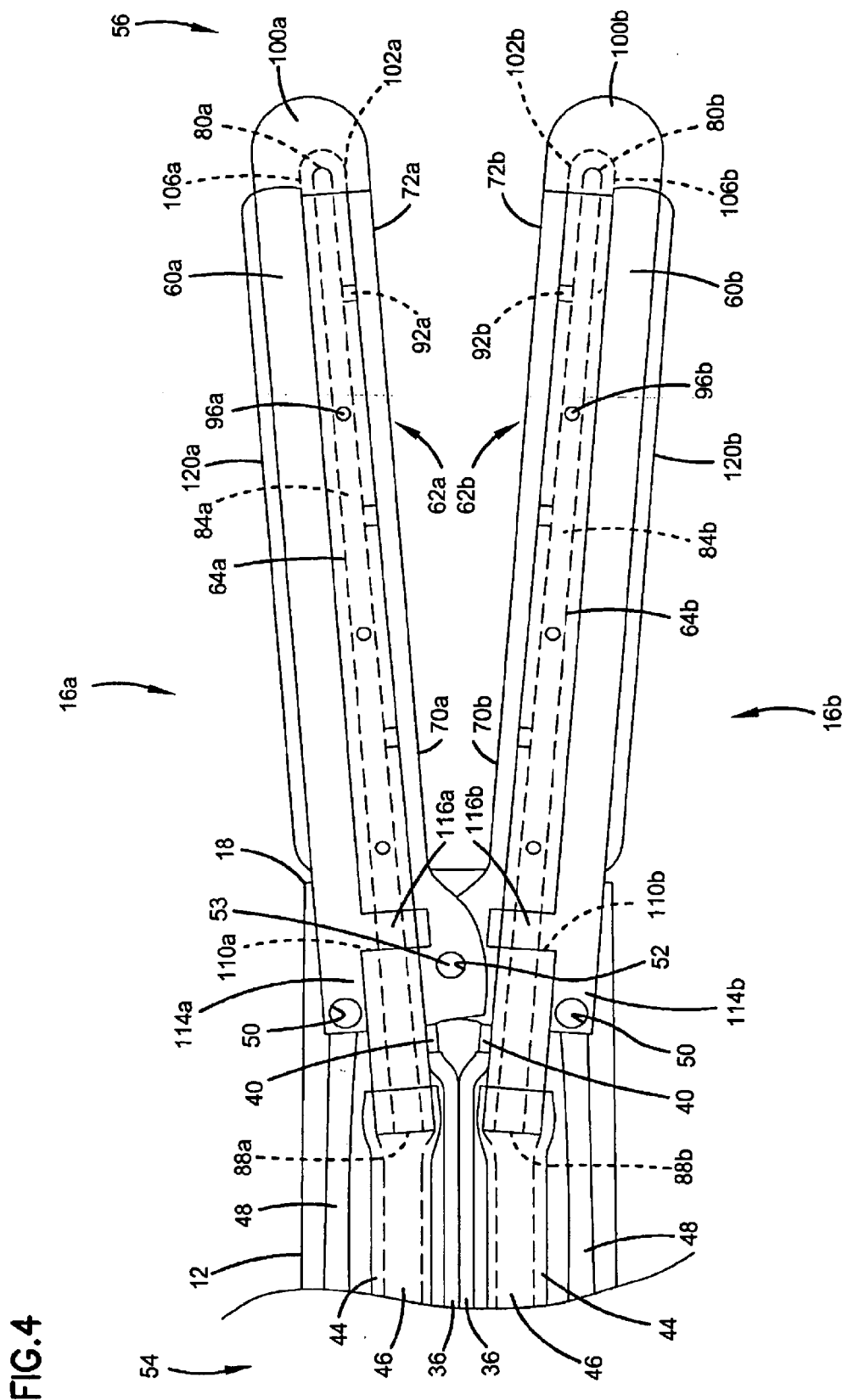
FIG. 4 is a close-up second side view of the tip portion of the device of FIG. 1.

As shown in FIGS. 3 and 4, jaws 16a, 16b are preferably connected to an actuator comprising rods 48 which move distally to close the jaws 16a, 16b with the movement of actuation lever 24 towards grip portion 26 of handle 22, and proximally with the opening of the jaws 16a, 16b with the movement of actuation lever 24 away from grip portion 26 of handle 22. More specifically, rods 48 preferably extend into moving pivot holes 50, with the rotation for each moving pivot hole 50 configured around a hinge comprising a fixed pin 53 extending through a fixed pivot hole 52 of shaft 12 and aligning holes in the jaws 16a, 16b.

Before continuing with the description of jaws 16a, 16b, it should be understood that, as used herein, the longitudinal dimension is relative to the length of the jaws 16a, 16b and is directed proximally and distally, the lateral dimension is relative to the width of the jaws 16a, 16b and is directed laterally (outward) or medially (inward), and the vertical dimension is relative to the height of the jaws 16a, 16b and is directed by opening and closing relative to one another.

Figure 6:
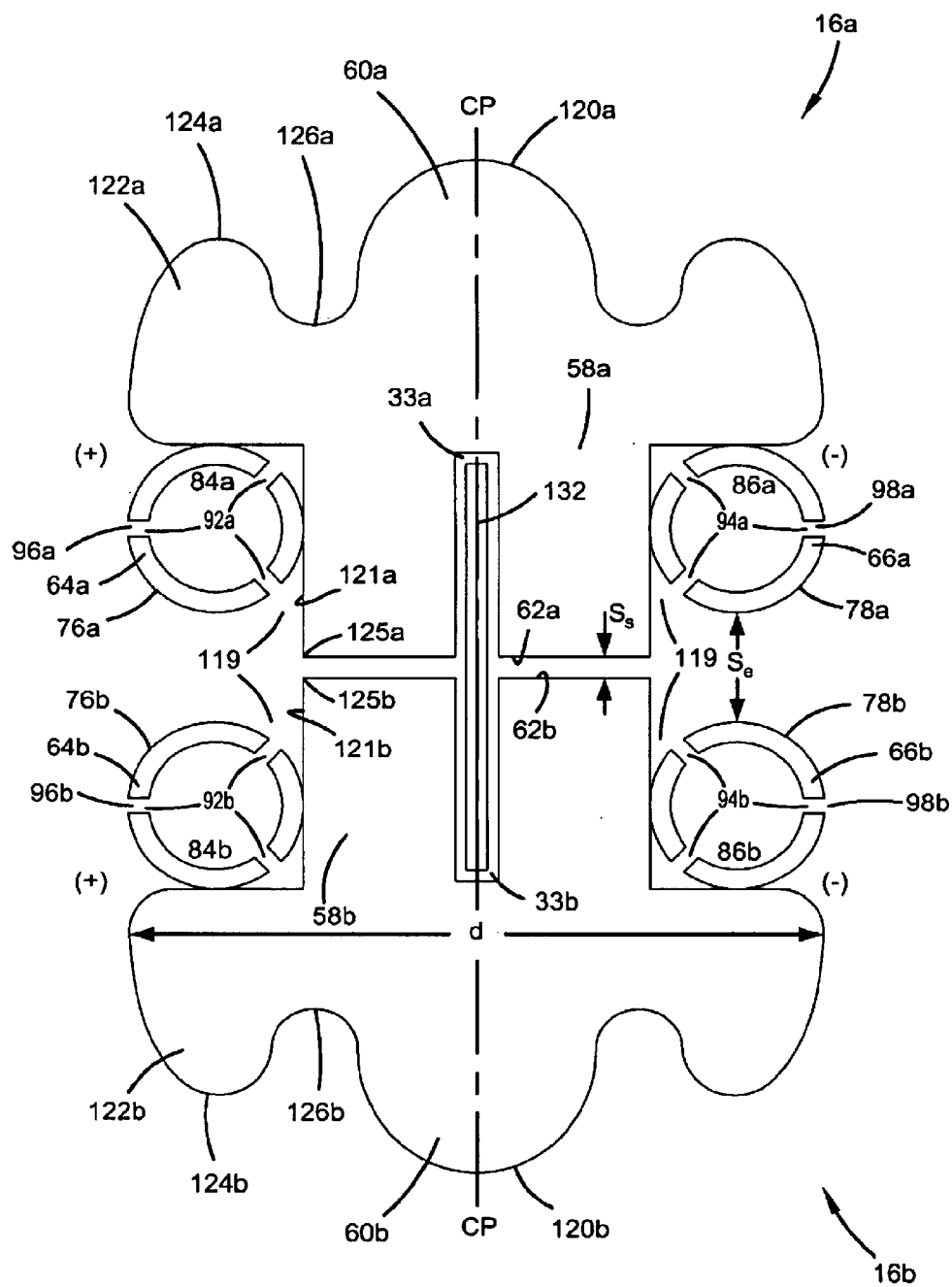
FIG. 6 is a cross-sectional view of the jaws 16a, 16b of the device of FIG. 1 taken along line 5—5 of FIG. 5.
Figure 16:
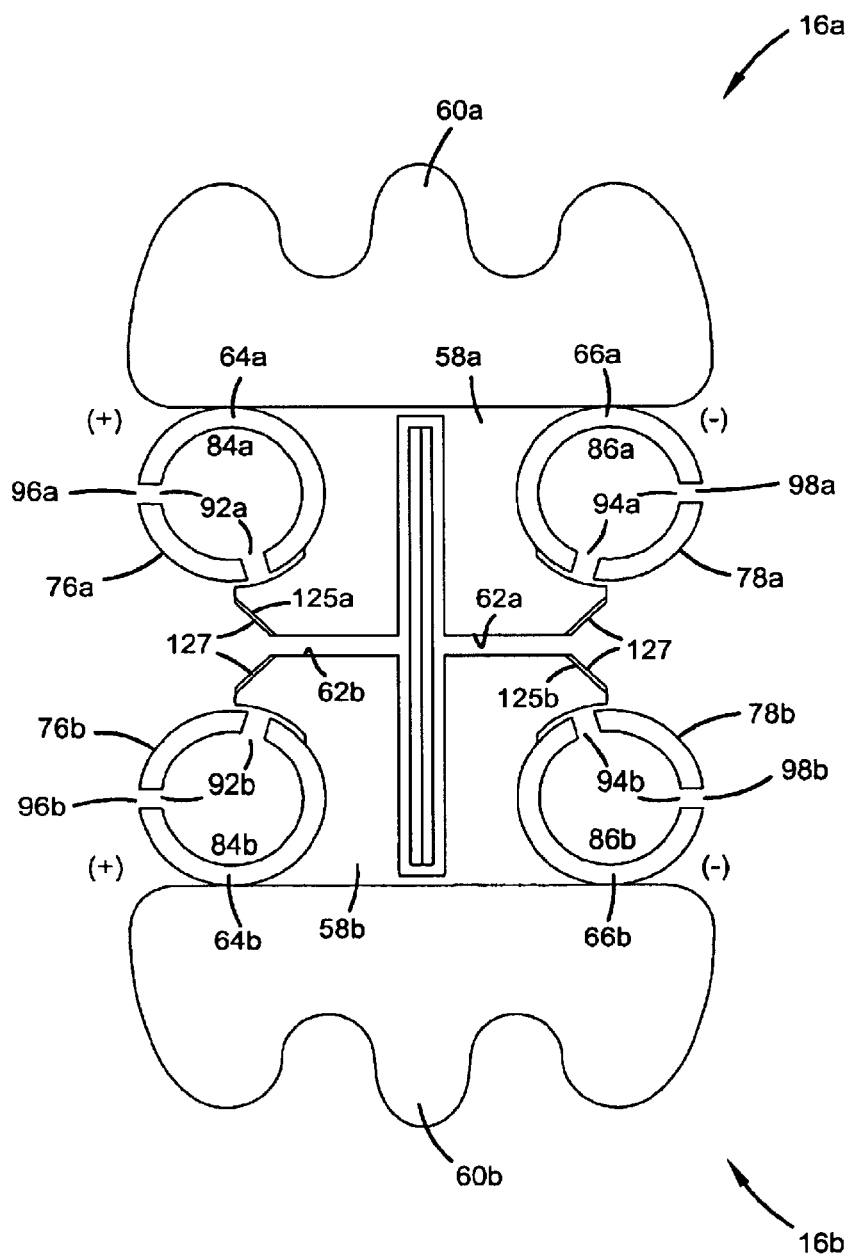
FIG. 16 is a cross-sectional view of another alternative embodiment of jaws 16a, 16b of the device of FIG. 1 taken along line 5—5 of FIG. 5.

As best shown in FIG. 6, jaws 16a, 16b preferably comprise elongated, substantially rectangular, centrally located tissue support members 58a, 58b which protrude from base portions 60a, 60b towards one another. As shown, support members 58a, 58b and base portions 60a, 60b may comprise a unitarily formed single piece. However, in alternative embodiments, as shown in FIG. 16, support members 58a, 58b and base portions 60a, 60b may comprise separately formed connected pieces.

As shown in FIG. 6, support members 58a, 58b provide anvils for directly opposing tissue grasping surfaces 62a, 62b. As shown in FIGS. 3 and 4, when the jaws 16a, 16b are open the grasping surfaces 62a, 62b converge proximally and diverge distally.

Grasping surfaces 62a, 62b further comprise electrically insulative surfaces which are preferably provided by support members 58a, 58b and base portions 60a, 60b comprising electrically insulating materials. In this manner, support members 58a, 58b and base portions 60a, 60b may be electrically insulated relative to electrodes 64a, 66a, 64b, 66b discussed in greater detail below.

In some embodiments, the electrically insulating material may comprise an electrically insulating polymer, either thermoplastic or thermoset, reinforced or unreinforced, filled or unfilled. Exemplary polymer materials include, but are not limited to, polyacetal (POM), polyamide (PA), polyamideimide (PAI), polyetheretherketone (PEEK), polyetherimide (PEI), polyethersulfone (PES), polyimide (PI), polyphenylenesulfide (PPS), polyphthalamide (PPA), polysulfone (PSO), polytetrafluoroethylene (PTFE) and syndiotactic polystyrene (SPS). More preferably, the electrically insulating polymer comprises either a liquid crystal polymer and, more particularly, an aromatic liquid crystal polyester which is reinforced with glass fiber, such as Vectra® A130 from Ticona, or Ultem® 10% glass filled polyetherimide from the General Electric Company. Exemplary reinforcement materials for polymers include, but are not limited to, glass fibers and boron fibers. Exemplary filler materials for polymers include mica, calcium carbonate and boron nitride. Reinforcement materials for the polymer material may be preferable for increased strength while filler materials may be preferable for increased heat resistance and/or thermal conductivity. Still other electrically insulating materials for support members 58a, 58b and base portions 60a, 60b may comprise electrically insulating ceramics such as boron nitride.

In order that heat may be transferred away from surfaces 62a, 62b during use of device 10, preferably the material for support members 58a, 58b and base portions 60a, 60b has a thermal conductivity $k_{tc}$ at 300° K (Kelvin) equal or greater than about 0.01 watt/cm° K. More preferably, the material for support members 58a, 58b and base portions 60a, 60b has a thermal conductivity $k_{tc}$ at 300° K (Kelvin) equal or greater than about 0.16 watt/cm° K. Even more preferably, the material for support members 58a, 58b and base portions 60a, 60b has a thermal conductivity $k_{tc}$ at 300° K (Kelvin) equal or greater than about 0.35 watt/cm° K.

In addition to grasping surfaces 62a, 62b comprising electrically insulating surfaces, preferably grasping surfaces 62a, 62b are substantially flat and provide for tissue removal there from. Furthermore, preferably grasping surfaces 62a, 62b also comprise hydrophobic surfaces to reduce the presence of fluid (e.g. conductive fluid 128 from fluid source 130; blood and other bodily fluids) on and between the grasping surfaces 62a, 62b, particularly those portions which are unoccupied by tissue during treatment.

Figure 17:
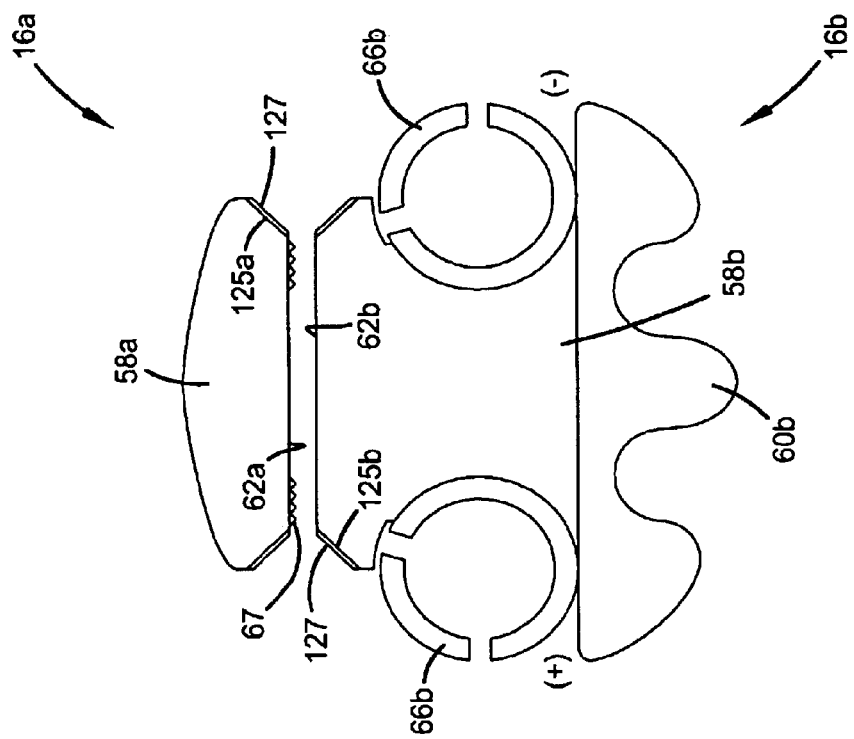
FIG. 17 is a cross-sectional view of another alternative embodiment of jaws 16a, 16b of the device of FIG. 1 taken along line 5—5 of FIG. 5.
Figure 18:
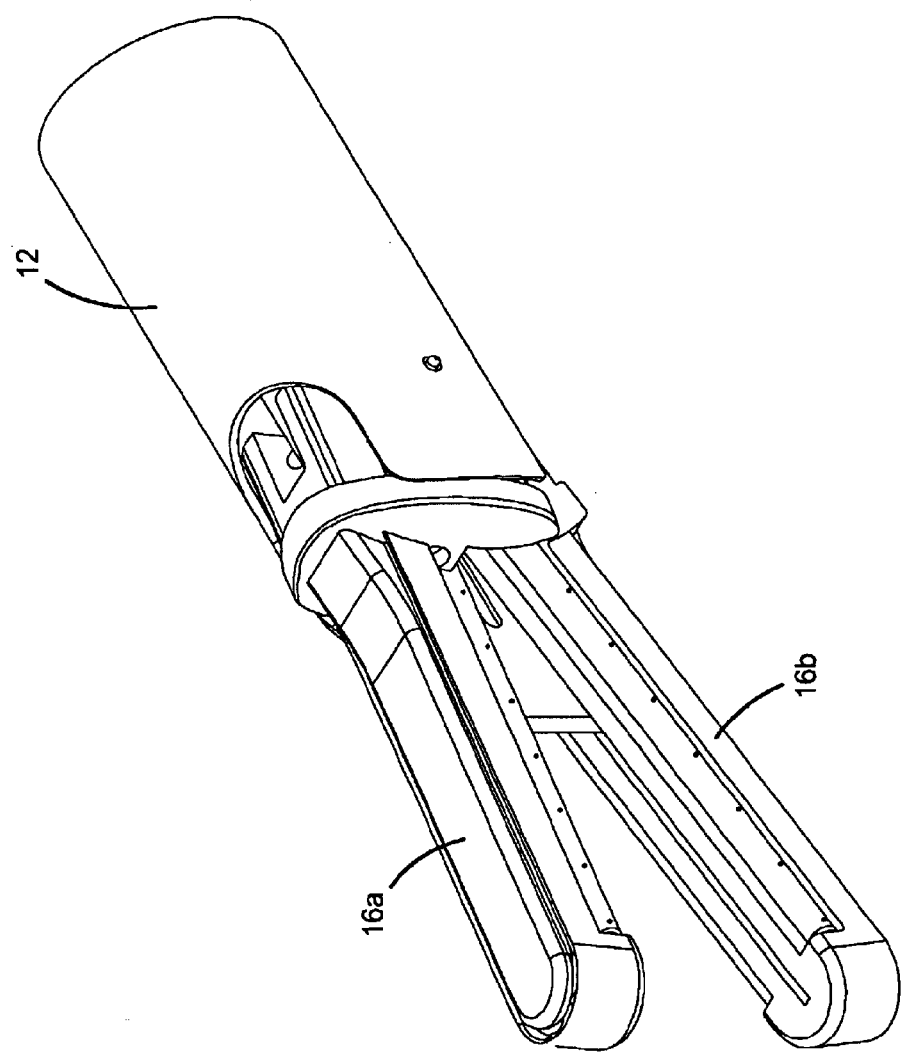
FIG. 18 is an assembled isometric view of another alternative embodiment of the tip portion and jaws 16a, 16b of the device of FIG. 1.
Figure 19:
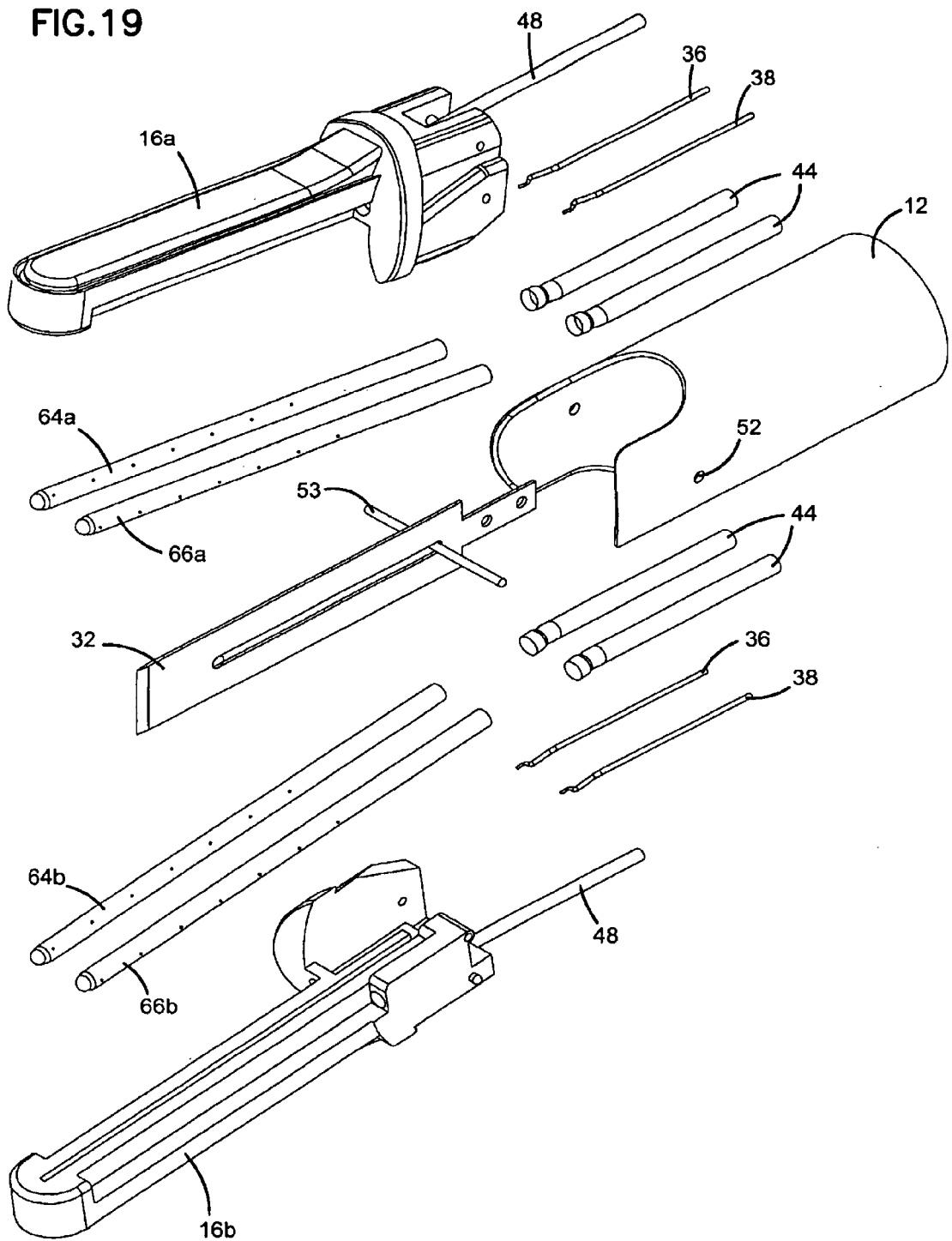
FIG. 19 is an exploded isometric view of the assembly of FIG. 18.

However, so that grasping surfaces 62a, 62b don't become so smooth that tissue therebetween may slide out, preferably the surfaces 62a, 62b are not highly polished smooth surfaces. In other words, preferably surfaces 62a, 62b have a surface roughness or asperity of surface in the range between and including about 20 microns to 500 microns where 10 microns is indicative of a polished surface. More preferably, 62a, 62b surfaces have a surface roughness in the range between and including about 25 microns to 250 microns. Furthermore, in various embodiments, surfaces 62a, 62b may comprise textured surfaces (a surface which is not smooth, but rather includes a raised pattern on it), such as a stipple textured surfaces. Also, in various embodiments, surfaces 62a, 62b may include serrations 67 (as shown in FIG. 17).

Figure 8:
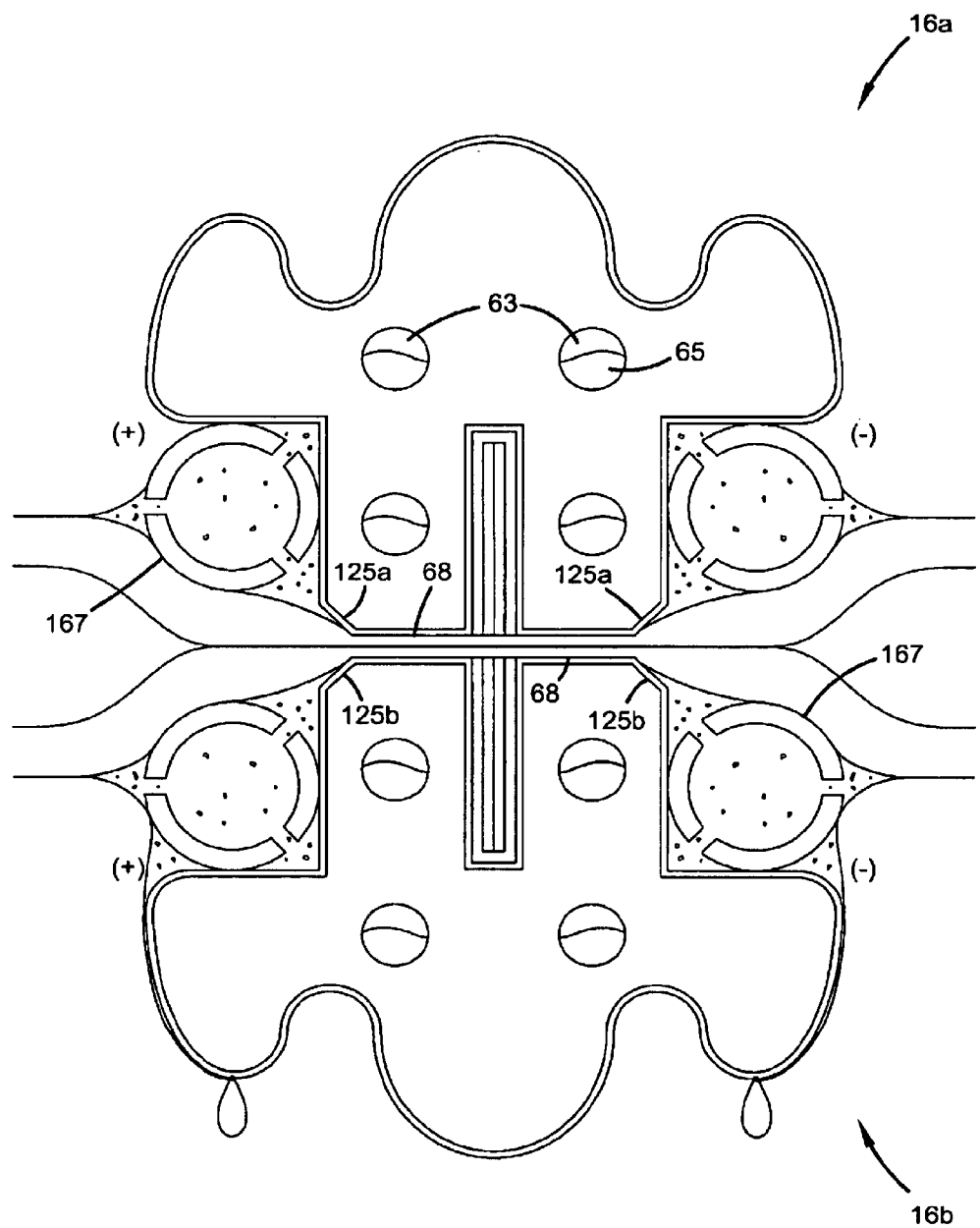
FIG. 8 is a cross-sectional view of an alternative embodiment of jaws 16a, 16b of the device of FIG. 1 taken along line 5—5 of FIG. 5.

In certain applications, it may be necessary to further increase the thermal conductivity of support members 58a, 58b and base portions 60a, 60b to better function as heat sinks to remove heat transferred to surfaces 62a, 62b from tissue there between. In alternative embodiments as shown in FIG. 8, jaws 16a, 16b comprise an electrically insulative, thin (less than about 0.5 mm thick) coating 68 which provides grasping surfaces 62a, 62b and which overlies support members 58a, 58b and base portions 60a, 60b, which comprise a material having a relatively higher thermal conductivity than the coating 68. For example, the insulative coating 68 may comprise a polymer coating applied over an underlying metal. In such an instance, it may be desirable to make the polymer coating 68 as thin as possible to maximize heat transfer into the underlying structure. An exemplary electrically insulative coating 68 may comprise a fluorinated polymer, such as polytetrafluoroethylene (PTFE). Exemplary metals which may underlie the electrically insulative coating are preferably non-corrosive, such as stainless steel, aluminum, titanium, silver, gold and platinum.

Preferably the material for support members 58a, 58b and base portions 60a, 60b underlying the coating 68 has a thermal conductivity $k_{tc}$ at 300° K (Kelvin) equal or greater than about 0.1 watt/cm° K. More preferably, the material for support members 58a, 58b and base portions 60a, 60b underlying the coating 68 has a thermal conductivity $k_{tc}$ at 300° K (Kelvin) equal or greater than about 1 watt/cm° K. Even more preferably, the material for support members 58a, 58b and base portions 60a, 60b underlying the coating 68 has a thermal conductivity $k_{tc}$ at 300° K (Kelvin) equal or greater than about 2 watt/cm° K.

As shown in FIG. 8, another structure which may be used to remove heat from support members 58a, 58b and base portions 60a, 60b comprises one or more heat pipes 63 containing a fluid 65 therein and connected to a heat exchanger as known in the art. Heat pipes 63 may be connected to a heat exchanger thermally isolated from the support members 58a, 58b and base portions 60a, 60b for removing heat from support members 58a, 58b and base portions 60a, 60b, or the heat pipe may be convectively cooled by fluid 128 provided to the jaws 16a, 16b.

As best shown in FIGS. 3–4 and 6, jaw 16a may include two electrodes 64a, 66a while jaw 16b may include two directly opposing electrodes 64b, 66b. Each electrode 64a, 66a, 64b, 66b is connectable to the generator 136 (as shown in FIG. 9), preferably by being electrically coupled via wire conductors 40, 42 of insulated wires 36, 38 which are ultimately electrically coupled to generator 136. Electrodes 64a, 66a, 64b, 66b preferably comprise a non-corrosive metal, such as stainless steel, aluminum, titanium, silver, gold or platinum.

As best shown in FIGS. 3 and 4, preferably electrodes 64a, 66a, 64b, 66b are orientated to extend along the length of the jaws 16a, 16b from the proximal end portions 70a, 70b to the distal end portions 72a, 72b of grasping surfaces 62a, 62b, preferably laterally outside the confines and borders of grasping surfaces 62a, 62b. Each electrode 64a, 66a, 64b, 66b is preferably configured to be substantially parallel to and equally spaced from support members 58a, 58b and grasping surfaces 62a, 62b along their respective lengths. However, in alternative embodiments, the electrodes 64a, 66a, 64b, 66b may not be substantially parallel, for example, to compensate for a varying width of grasping surfaces 62a, 62b or tissue thickness.

Preferably electrodes 64a, 64b comprise electrical source electrodes while electrodes 66a, 66b comprise counter electrodes. As shown in FIG. 6, source electrodes 64a, 64b are shown with the positive electrical sign (+) while counter electrodes 66a, 66b are shown with the negative electrical sign (−). Thus, the source electrodes 64a, 64b and counter electrodes 66a, 66b have different electrical potentials. Also as shown in FIG. 6, each jaw 16a, 16b may comprise one electrical source electrode and one electrical counter electrode, with the two electrodes on each of the jaws 16a, 16b configured to have the same polarity with the directly opposing electrodes on the opposite jaw.

Given the above configuration, electrodes 64a, 66a, 64b, 66b are configured such that electrical current flowing in the tissue between grasping surfaces 62a, 62b will flow across (substantially parallel to) the grasping surfaces 62a, 62b. With electrodes 64a, 66a, 64b, 66b in such a configuration, four possible electrical paths are created between: (1) electrodes 64a and 66a; (2) electrodes 64a and 66b; (3) electrodes 64b and 66b; and (4) electrodes 64b and 66a.

Figure 7:
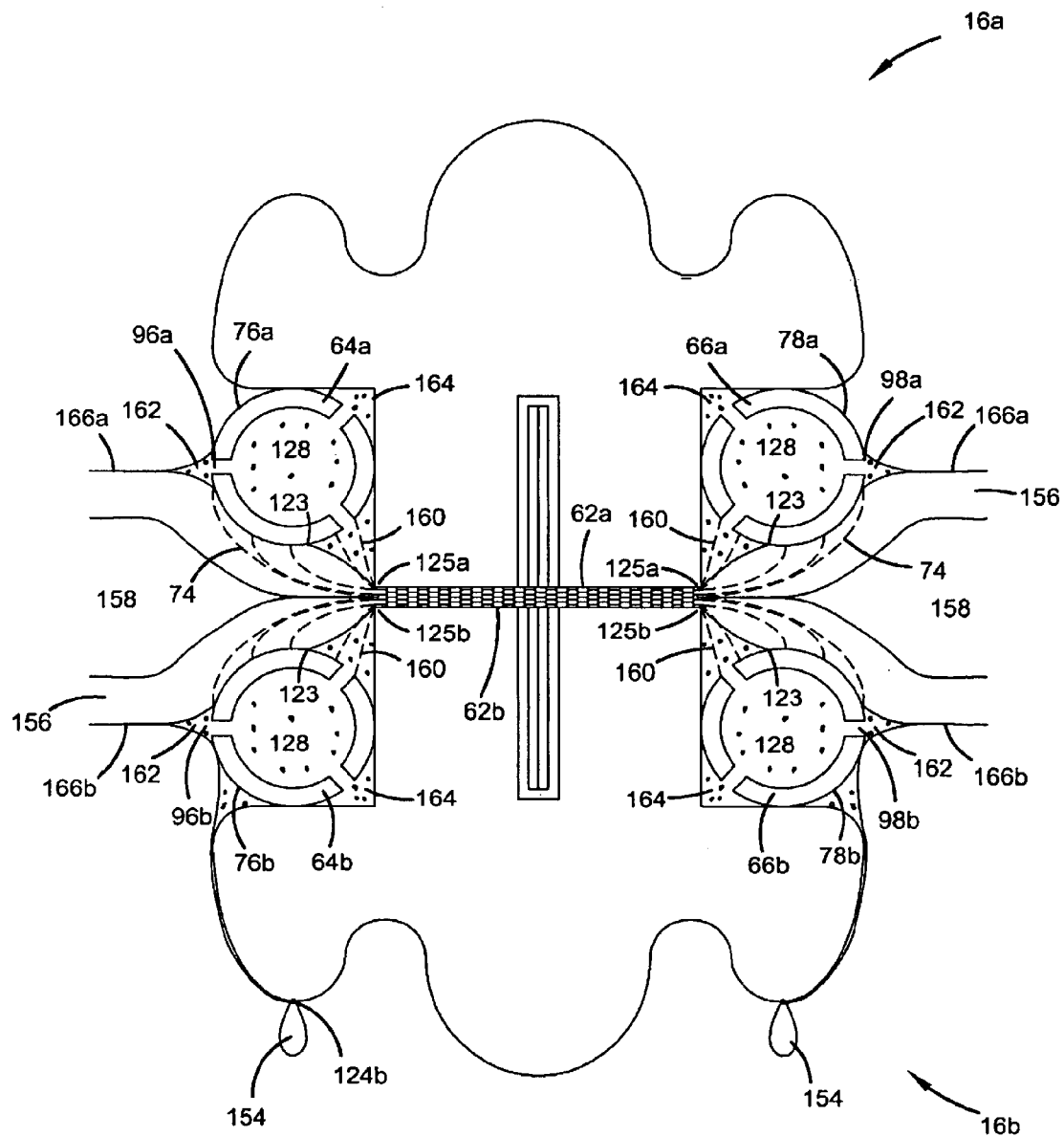
FIG. 7 is a cross-sectional view of the jaws 16a, 16b of the device of FIG. 1 with tissue and fluid taken along line 5—5 of FIG. 5.

The creation of certain of these electrical paths is denoted by electrical field lines 74 in FIG. 7. It should be noted that the contour of electrical field lines 74 is exemplary. Furthermore, particularly outside grasping surfaces 62a, 62b, it should be noted that the electrical field lines 74 are exemplary as to where electrical current is expected to flow, and not necessarily where the greatest current density is expected to reside.

Figure 10:
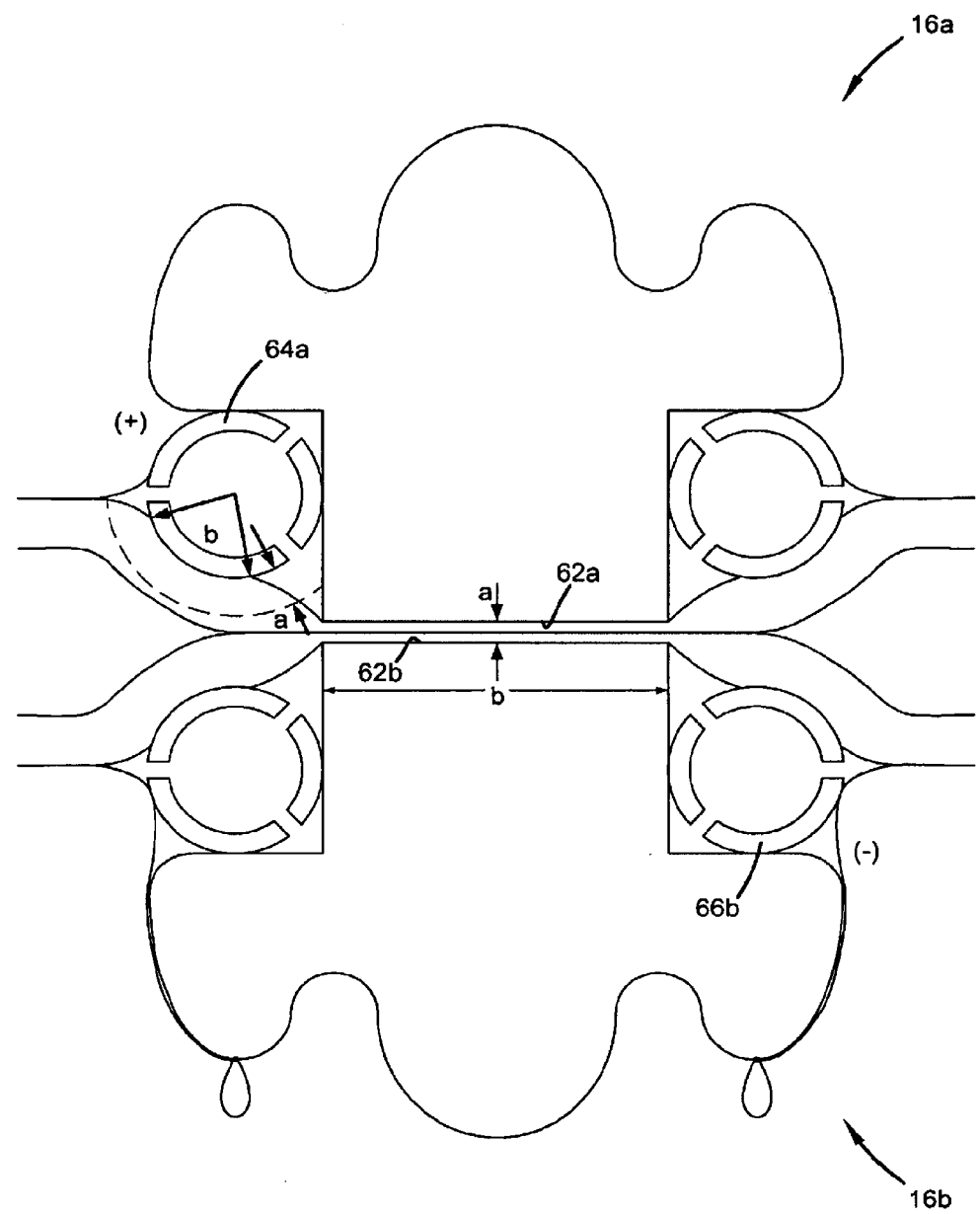
FIG. 10 is another cross-sectional view of the jaws 16a, 16b of the device of FIG. 1 with tissue and fluid taken along line 5—5 of FIG. 5.

Returning to FIG. 6, it is to be understood that, within the scope of the invention, only one pair of electrodes is required for the invention (as shown in FIG. 17). Furthermore, it is to be understood that, within the scope of the invention, where only one electrode pair is utilized, the electrodes do not have to be on the same jaw (as shown in FIG. 10). In other words, the electrodes, while still configured outside of and separated from opposing edges of grasping surfaces 62a, 62b, may be configured with one electrode on each jaw (e.g. diagonally arranged). Thus, a suitable electrode pair may comprise any pair of electrodes above (i.e. 64a and 66a; 64a and 66b; 64b and 66b; 64b and 66a) which create any one of the four electrical paths identified.

As indicated above, preferably grasping surfaces 62a, 62b also comprise hydrophobic surfaces to reduce the presence of fluid on and between grasping surfaces 62a, 62b, particularly portions which are unoccupied by tissue. Reducing the presence of fluid on unoccupied portions of surfaces 62a, 62b is desirable to inhibit, and more preferably minimize or prevent, the formation of a conductive fluid shunt. In other words, if conductive fluid forms a bridge across the width of surfaces 62a, 62b, and the bridge connects an electrode pair configured to create an electrical path (i.e. 64a and 66a; 64a and 66b; 64b and 66b; 64b and 66a), an electrical path through the conductive fluid bridge is created parallel to the electrical path through tissue. Consequently, a portion of the electrical energy intended to be provided to tissue is diverted through the conductive fluid bridge and bypasses the tissue. This loss of energy can increase the time required to treat tissue.

Other than surfaces 62a, 62b comprising hydrophobic surfaces, in order to reduce the presence of fluid on and between the unoccupied portions of grasping surfaces 62a, 62b of device 10, preferably the contact angle θ of fluid droplets, particularly of fluid 128, on grasping surfaces 62a, 62b is about 30 degrees or greater after the droplet has stabilized from initial placement thereon. More preferably, the contact angle θ of fluid droplets, particularly of fluid 128, on grasping surfaces 62a, 62b is about 45 degrees or greater. More preferably, the contact angle θ of fluid droplets, particularly of fluid 128, on grasping surfaces 62a, 62b is about 60 degrees or greater. Even more preferably, the contact angle θ of fluid droplets, particularly of fluid 128, on grasping surfaces 62a, 62b is about 75 degrees or greater. Most preferably, the contact angle θ of fluid droplets, particularly of fluid 128, on grasping surfaces 62a, 62b is about 90 degrees or greater.

Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $\gamma_{LV} \cos \theta = \gamma_{SV} - \gamma_{SL}$ where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting.

For clarification, while it is known that the contact angle θ may be defined by the preceding equation, in reality contact angle θ is determined by a various models to an approximation. According to publication entitled "Surface Energy Calculations" (dated Sep. 13, 2001) from First Ten Angstroms (465 Dinwiddie Street, Portsmouth, Va. 23704), there are five models which are widely used to approximate contact angle θ and a number of others which have small followings. The five predominate models and their synonyms are: (1) Zisman critical wetting tension; (2) Girifalco, Good, Fowkes, Young combining rule; (3) Owens, Wendt geometric mean; (4) Wu harmonic mean; and (5) Lewis acid/base theory. Also according to the First Ten Angstroms publication, for well-known, well characterized surfaces, there can be a 25% difference in the answers provided for the contact angle θ by the models. Any one of the five predominate models above which calculates a contact angle θ recited by a particular embodiment of the invention should be considered as fulfilling the requirements of the embodiment, even if the remaining four models calculate a contact angle θ which does not fulfill the recitation of the embodiment.

As best shown in FIGS. 3–4 and 6, in certain embodiments, each electrode 64a, 66a, 64b, 66b comprises an elongated structure extending longitudinally on jaws 16a, 16b. As best shown in FIG. 6, electrodes 64a, 66a, 64b, 66b preferably each comprise generally tubular structures having cylindrical outer surfaces 76a, 78a, 76b, 78b with substantially uniform diameters. Preferably, electrodes 64a, 66a, 64b, 66b have a cross-sectional dimension (e.g. diameter) in the range between and including about 0.1 mm to 4 mm and more preferably have a diameter in the range between and including about 1 mm to 2 mm.

As shown in FIGS. 3 and 4, in certain embodiments, electrodes 64a, 66a, 64b, 66b have distal end wall portions 80a, 82a, 80b, 82b comprising generally domed shapes. In this manner, the distal ends of electrodes 64a, 66a, 64b, 66b preferably provide smooth, blunt contour outer surfaces which are devoid of sharp edges.

It should be understood that the structure providing electrodes 64a, 66a, 64b, 66b need not wholly comprise an electrically conductive material. In other words, for example, only the tissue interacting/treating surfaces 76a, 78a, 76b, 78b of electrodes 64a, 66a, 64b, 66b need be electrically conductive. Thus, for example, the exemplary tubular structure for electrodes 64a, 66a, 64b, 66b may comprise an electrically conductive coating, such as metal, overlying an electrically insulative material, such as a polymer or ceramic.

Figure 5:
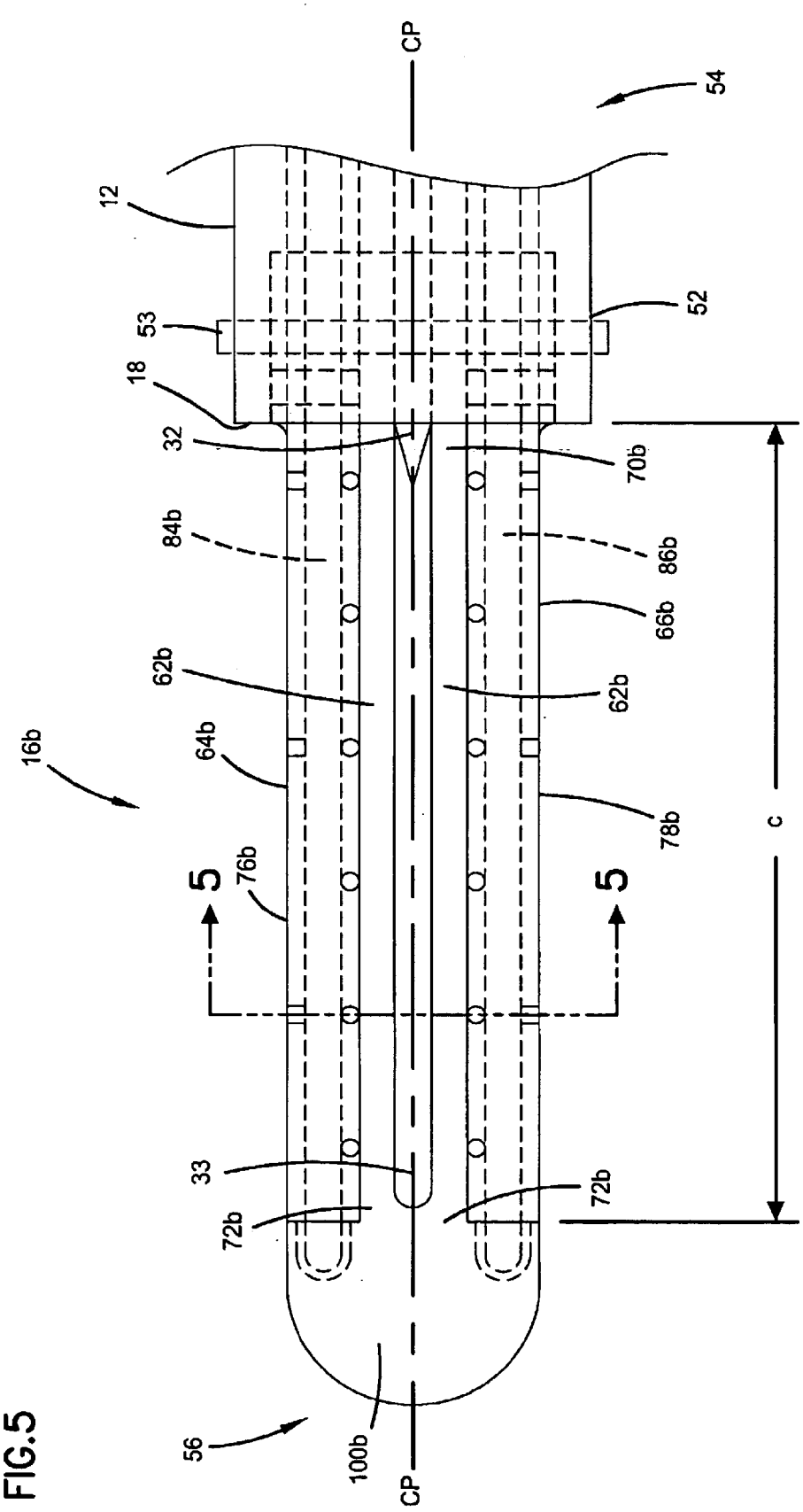
FIG. 5 is a close-up top view of the tip portion of the device of FIG. 1 with jaw 16a removed.

As best shown by FIG. 5, the surfaces 76a, 78a, 76b, 78b of electrodes 64a, 66a, 64b, 66b for treating tissue preferably terminate proximal to the distal end of a cutting mechanism 32 (where a cutting mechanism is employed), which preferably comprises a planar blade with a sharpened distal end. Cutting mechanism 32 is extendable from the distal end 18 of shaft 12 and travels on and along a center plane CP that is perpendicular to grasping surfaces 62a, 62b (as shown in FIG. 6) and segments the jaws 16a, 16b into opposing first and second sides (i.e. left-side portion and right-side portion), which are symmetrical in certain embodiments. Cutting mechanism 32 travels both longitudinally proximally and distally in an elongated travel slot 33a, 33b. Cutting mechanism 32 is particularly used with endoscopic versions of device 10. In this manner, device 10 is configured to treat tissue proximal to the distal end of the cutting mechanism 32 which reduces the possibility of cutting untreated or partially treated tissue with cutting mechanism 32 when activated.

In contrast to the contact angle θ of fluid droplets on device grasping surfaces 62a, 62b most preferably being about 90 degrees or greater, preferably the contact angle θ of fluid droplets, particularly fluid 128, on surfaces 76a, 78a, 76b, 78b of electrodes 64a, 66a, 64b, 66b is about 90 degrees or less after the droplet has stabilized from initial placement thereon. More preferably, the contact angle θ of fluid droplets, particularly fluid 128, on surfaces 76a, 78a, 76b, 78b of electrodes 64a, 66a, 64b, 66b is about 75 degrees or less. More preferably, the contact angle θ of fluid droplets, particularly fluid 128, on surfaces 76a, 78a, 76b, 78b of electrodes 64a, 66a, 64b, 66b is about 60 degrees or less. Even more preferably, the contact angle θ of fluid droplets, particularly fluid 128, on surfaces 76a, 78a, 76b, 78b of electrodes 64a, 66a, 64b, 66b is about 45 degrees or less. Most preferably, the contact angle θ of fluid droplets, particularly fluid 128, on surfaces 76a, 78a, 76b, 78b of electrodes 64a, 66a, 64b, 66b is about 30 degrees or less.

Preferably fluid 128 (shown in FIGS. 7 and 9) wets the surfaces 76a, 78a, 76b, 78b of electrodes 64a, 66a, 64b, 66b such that the fluid 128 forms a thin, continuous film coating at least partially thereon and does not form isolated rivulets or circular beads which freely run off the surfaces 76a, 78a, 76b, 78b of electrodes 64a, 66a, 64b, 66b.

As shown in FIG. 7, each jaw 16a, 16b preferably comprises at least one fluid flow passage and outlet configured to provide fluid 128 to surfaces 166a, 166b of tissue 156 and/or surfaces 76a, 78a, 76b, 78b of electrodes 64a, 66a, 64b, 66b, and/or therebetween. To minimize complexity, preferably a portion of an electrode forms at least a portion of the fluid flow passage.

As best shown in FIGS. 3–4 and 6, in certain embodiments, each electrode 64a, 66a, 64b, 66b is hollow and comprises a rectilinear, longitudinally extending, cavity forming a central (primary) fluid flow passage 84a, 86a, 84b, 86b for fluid 128. To minimize complexity, each electrode 64a, 66a, 64b, 66b may be formed from hypodermic tubing and the central flow passages 84a, 86a, 84b, 86b comprise the lumens of the hypodermic tubing. Furthermore, as shown in FIG. 6, the hypodermic tubing provides a cornerless electrode to distribute electrical energy to the tissue more uniformly and avoid concentrated edge effects typically encountered with the transmission of electrical energy through electrodes having sharp edges.

As best shown in FIGS. 3–4 and 5, each central flow passage 84a, 86a, 84b, 86b is preferably orientated to extend along the length of the jaws 16a, 16b from the proximal end portions 70a, 70b to the distal end portions 72a, 72b of grasping surfaces 62a, 62b of the jaws 16a, 16b, preferably laterally outside grasping surfaces 62a, 62b. Also, as shown, each central flow passage 84a, 86a, 84b, 86b is preferably configured to extend along the length of the jaws 16a, 16b coextensively with electrodes 64a, 66a, 64b, 66b. Furthermore, as shown, each central flow passage 84a, 86a, 84b, 86b is preferably configured to be substantially parallel to and equally spaced from support members 58a, 58b and grasping surfaces 62a, 62b along their respective lengths.

As shown in FIGS. 3 and 4, preferably each central flow passage 84a, 86a, 84b, 86b has a central flow passage fluid entrance opening 88a, 90a, 88b, 90b located near the proximal end 54 of jaws 16a, 16b. Also as shown, each central flow passage 84a, 86a, 84b, 86b is connectable to the fluid source 130 (shown in FIG. 9), preferably by being fluidly coupled with the passage 46 of flexible tube 44 which is ultimately fluidly coupled to fluid source 130.

In addition to central flow passages 84a, 86a, 84b, 86b, as best shown in FIG. 6, the flow passages also preferably comprise at least one rectilinear, radially directed, side (secondary) fluid flow passage 92a, 94a, 92b, 94b which is fluidly coupled to each central flow passage 84a, 86a, 84b, 86b. More preferably, as shown in FIGS. 3–6, each fluid flow passage preferably comprises a plurality of side flow passages 92a, 94a, 92b, 94b which are defined and spaced preferably both longitudinally and circumferentially around electrodes 64a, 66a, 64b, 66b and central flow passages 84a, 86a, 84b, 86b. Also preferably, as shown the side flow passages 92a, 94a, 92b, 94b are defined and spaced from the proximal end portions 70a, 70b to the distal end portions 72a, 72b of grasping surfaces 62a, 62b of each jaw 16a, 16b.

Also as shown, side flow passages 92a, 94a, 92b, 94b preferably each have a cross-sectional dimension, more specifically diameter, and corresponding cross-sectional area, less than the portion of central flow passage 84a, 86a, 84b, 86b from which fluid 128 is provided. Also as shown, the side flow passages 92a, 94a, 92b, 94b extend through the cylindrical portion of the electrodes 64a, 66a, 64b, 66b and are preferably formed substantially at a right angle (e.g. within about 10 degrees of a right angle) to the central flow passages 84a, 86a, 84b, 86b both longitudinally and circumferentially. Also as shown, the side flow passages 92a, 94a, 92b, 94b are preferably formed substantially at a right angle to the tissue interacting/treating cylindrical surfaces 76a, 78a, 76b, 78b of electrodes 64a, 66a, 64b, 66b.

Preferably, side flow passages 92a, 94a, 92b, 94b extend from central flow passages 84a, 86a, 84b, 86b to side flow passage fluid exit openings 96a, 98a, 96b, 98b located on surfaces 76a, 78a, 76b, 78b. More preferably, side flow passages 92a, 94a, 92b, 94b and associated side flow passage fluid exit openings 96a, 98a, 96b, 98b are defined and spaced both longitudinally and circumferentially around the surfaces 76a, 78a, 76b, 78b, along the length of the jaws 16a, 16b from the proximal end portions 70a, 70b to the distal end portions 72a, 72b of grasping surfaces 62a, 62b of the jaws 16a, 16b.

As shown in FIGS. 3–6, preferably the plurality of side flow passages 92a, 94a, 92b, 94b, and corresponding side flow passage fluid exit openings 96a, 98a, 96b, 98b are configured to form both longitudinal and circumferential straight rows, and are preferably uniformly spaced relative to one another. Also preferably, the plurality of side flow passages 92a, 94a, 92b, 94b are configured to distribute fluid flow exiting from side flow passage fluid exit openings 96a, 98a, 96b, 98b substantially uniformly.

Preferably, side flow passages 92a, 94a, 92b, 94b have a cross-sectional dimension (e.g. diameter) in the range between and including about 0.1 mm to 1 mm and more preferably have a diameter in the range between and including about 0.15 mm to 0.2 mm. As for central flow passages 84a, 86a, 84b, 86b, preferably central fluid flow passages 84a, 86a, 84b, 86b have a cross-sectional dimension (e.g. diameter) in the range between and including about 0.2 mm to 2 mm and more preferably have a diameter in the range between and including about 0.5 mm to 1 mm.

As shown in FIGS. 3 and 4, distal wall portions 80a, 82a, 80b, 82b at least partially provide and define the distal ends of central flow passages 84a, 86a, 84b, 86b, respectively. Also as shown, preferably wall portions 80a, 82a, 80b, 82b completely provide and define the distal ends of central flow passages 84a, 86a, 84b, 86b such that the distal ends of the central fluid flow passages 84a, 86a, 84b, 86b preferably comprise blind ends. Consequently, the central flow passages 84a, 86a, 84b, 86b preferably do not continue completely through electrodes 64a, 66a, 64b, 66b. Rather, the distal ends of the central flow passages 84a, 86a, 84b, 86b terminate within the confines of the electrodes 64a, 66a, 64b, 66b and are closed by a structure, here wall portions 80a, 82a, 80b, 82b forming the distal ends of central flow passages 84a, 86a, 84b, 86b.

However, wall portions 80a, 82a, 80b, 82b need not completely occlude and define the distal ends of central flow passages 84a, 86a, 84b, 86b. In other words, rather than extending only partially through electrodes 64a, 66a, 64b, 66b, central flow passages 84a, 86a, 84b, 86b may extend completely through electrodes 64a, 66a, 64b, 66b and have a distal end opening. However, in such an instance, a wall portions 80a, 82a, 80b, 82b should substantially occlude and inhibit fluid 128 from exiting from the central flow passage distal end exit opening. With regards to this specification, occlusion of a central flow passage distal end exit opening and the corresponding inhibiting of flow from exiting from the central flow passage distal end exit opening should be considered substantial when the occlusion and corresponding inhibiting of flow results in increased flow from the side flow passage fluid exit openings 96a, 98a, 96b, 98b of side flow passages 92a, 94a, 92b, 94b. In other words, wall portions 80a, 82a, 80b, 82b merely need to function as fluid flow diverters and redirect a portion of the fluid 128 coming in contact therewith from flowing parallel with the longitudinal axis of the central fluid flow passages 84a, 86a, 84b, 86b to flowing radially from the longitudinal axis through side flow passages 92a, 94a, 92b, 94b.

Figure 20:
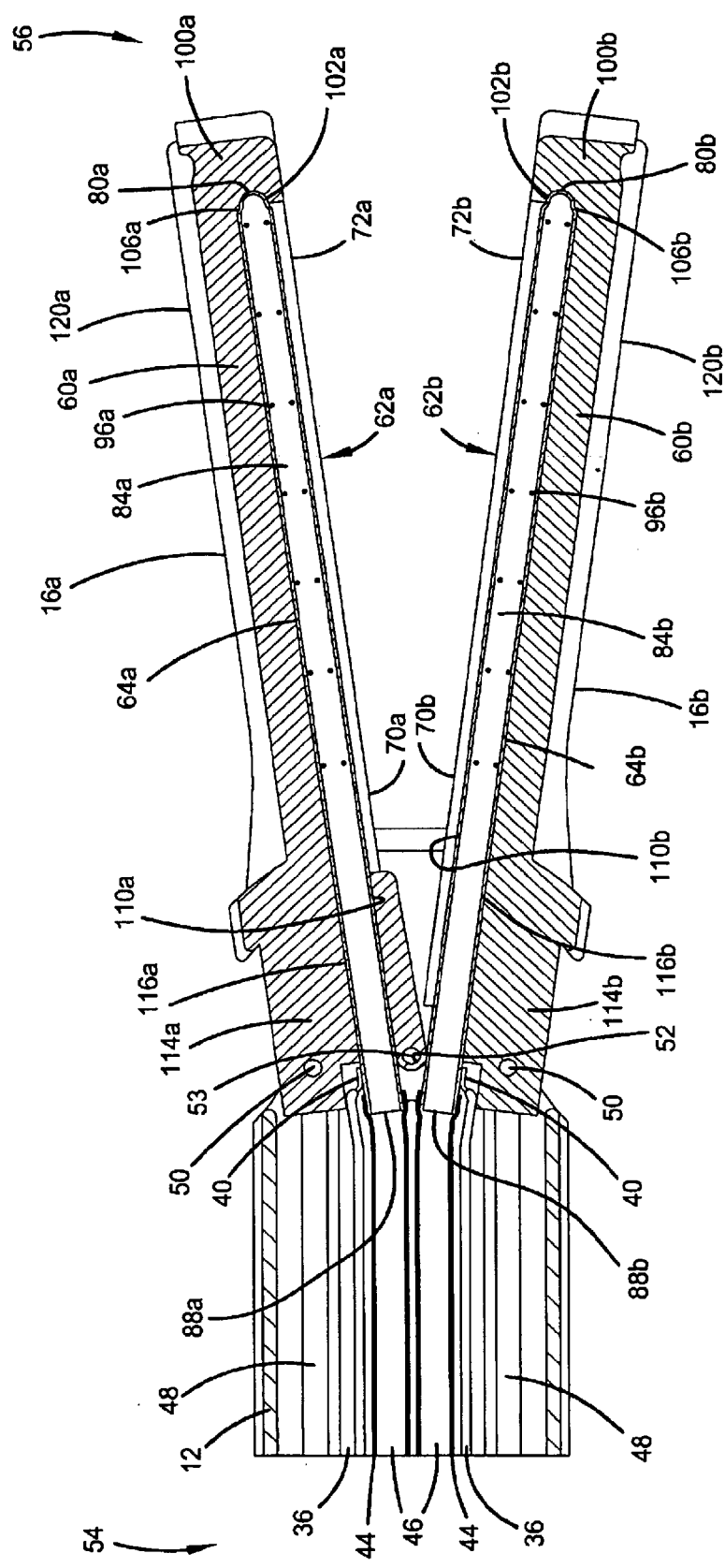
FIG. 20 is a first side cross-sectional view of the tip portion of FIG. 18.
Figure 21:
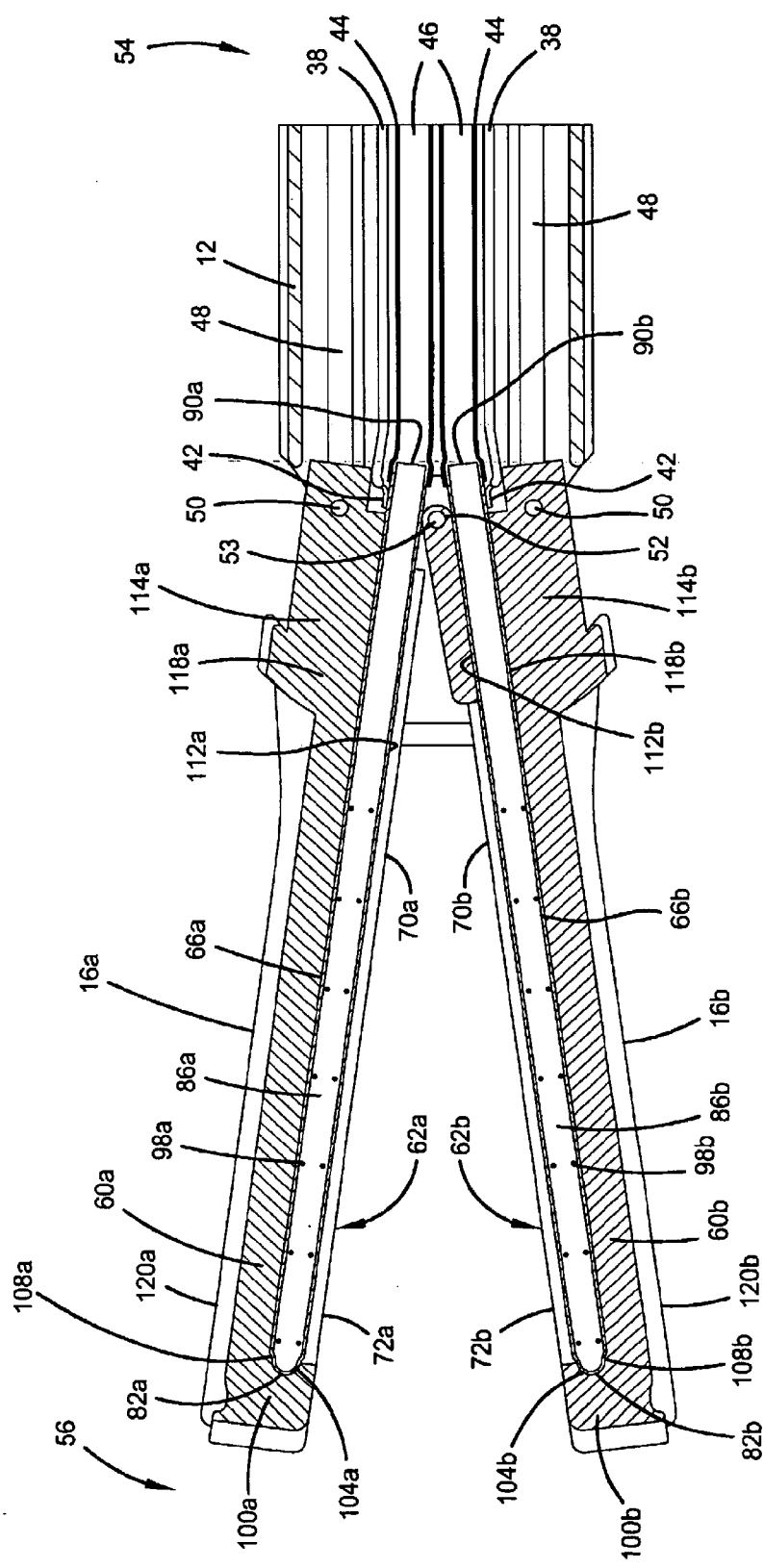
FIG. 21 is a second side cross-sectional view of the tip portion of FIG. 18.

As shown, wall portions 80a, 82a, 80b, 82b are preferably integral, and more preferably unitary, with the remainder of electrodes 64a, 66a, 64b, 66b. Where electrodes 64a, 66a, 64b, 66b are provided by hypodermic tubing, closure or occlusion of the central flow passages 84a, 86a, 84b, 86b may be accomplished by welding or crimping (as best shown in FIGS. 20 and 21) a previously open distal end of the hypodermic tubing. In alternative embodiments, wall portions 80a, 82a, 80b, 82b may be provided by a separate plug inserted into the distal end portion of central flow passages 84a, 86a, 84b, 86b. Also in alternative embodiments, wall portions 80a, 82a, 80b, 82b may be provided by distal end portions 100a, 100b of jaws 16a, 16b.

Jaws 16a, 16b preferably comprise at least one connector portion for attaching electrodes 64a, 66a, 64b, 66b thereto. As shown in FIGS. 3 and 4, the connector portions preferably comprise receptacles 102a, 104a, 102b, 104b connected laterally adjacent to the support members 58a, 58b and located at the distal end portions 100a, 100b of jaws 16a, 16b. As shown in FIGS. 3 and 4, the connector portions for attaching electrodes 64a, 66a, 64b, 66b to jaws 16a, 16b are vertically adjacent base portions 60a, 60b and protrude from base portions 60a, 60b towards one another in the same manner as support members 58a, 58b.

Preferably, receptacles 102a, 104a, 102b, 104b are formed unitarily with support members 58a, 58b as single pieces and provide a housing comprising cylindrical blind holes for containing distal end cylindrical portions 106a, 108a, 106b, 108b of electrodes 64a, 66a, 64b, 66b. The distal end cylindrical portions 106a, 108a, 106b, 108b of the electrodes 64a, 66a, 64b, 66b located in the receptacles 102a, 104a, 102b, 104b preferably form an interference fit within the receptacles 102a, 104a, 102b, 104b to inhibit removal therefrom.

Preferably jaws 16a, 16b also comprise a second connector portion for attaching T electrodes 64a, 66a, 64b, 66b thereto. As shown in FIGS. 3 and 4, the connector portions preferably comprise receptacles 110a, 112a, 110b, 112b connected laterally adjacent to the support members 58a, 58b and located at the proximal end portions 114a, 114b of jaws 16a, 16b.

Preferably, receptacles 110a, 112a, 110b, 112b are also formed unitarily with support members 58a, 58b as single pieces and provide a housing comprising cylindrical through holes for containing proximal end cylindrical portions 116a, 118a, 116b, 118b of electrodes 64a, 66a, 64b, 66b. The proximal end cylindrical portions 116a, 118a, 116b, 118b of the electrodes 64a, 66a, 64b, 66b located in the receptacles 110a, 112a, 110b, 112b preferably form an interference fit within the receptacles 110a, 112a, 110b, 112b to inhibit removal therefrom.

In certain situations tissue laterally outside grasping surfaces 62a, 62b may be compressed by a portion of the jaws 16a, 16b, particularly electrodes 64a, 66a, 64b, 66b. In order to concentrate a great majority of the electrical power converted to heat in the tissue located in the medial portion of grasping surfaces 62a, 62b (equal to about the middle one-third of the width) preferably the tissue outside grasping surfaces 62a, 62b will be compressed to a lesser extent (e.g. percentage) than the tissue between grasping surfaces 62a, 62b. Consequently, as shown in FIG. 6, preferably surfaces 76a, 78a, 76b, 78b of electrodes 64a, 66a, 64b, 66b are vertically recessed and, more particularly, stepped down relative to surfaces 62a, 62b such that the minimum separation distance Se between directly opposing electrode surfaces 76a, 76b and 78a, 78b is greater than the minimum separation distance SS between grasping surfaces 62a, 62b. As a result, tissue which may be partially compressed between surfaces 76a, 76b and 78a, 78b, for example, will be heated less than tissue in the medial portion of surfaces 62a, 62b which is more fully compressed. However, as shown in FIG. 7, surfaces 76a, 78a, 76b, 78b should not be stepped down relative to surfaces 62a, 62b such that electrical coupling is not maintained with surfaces 166a, 166b of tissue 156 and fluid couplings 160 and 162 (discussed in greater detail below) are unable to couple the surfaces 76a, 78a, 76b, 78b with surfaces 166a, 166b of tissue 156.

Continuing with FIG. 6, surfaces 76a, 78a, 76b, 78b of electrodes 64a, 66a, 64b, 66b are preferably configured such that the portion of surfaces 76a, 78a, 76b, 78b closest to grasping surfaces 62a, 62b is remotely located and spatially separated from grasping surfaces 62a, 62b. More specifically, as shown, the portion of surfaces 76a, 78a, 76b, 78b closest grasping surfaces 62a, 62b is remotely separated both laterally and vertically from grasping surfaces 62a, 62b. Furthermore, as shown, preferably the portion of surfaces 76a, 78a, 76b, 78b closest to grasping surfaces 62a, 62b is remotely separated from grasping surfaces 62a, 62b by air gaps 119 (which are ultimately occupied by fluid couplings 160 discussed below).

As shown in FIG. 6, the air gaps 119 are defined by two sides relative to device 10. More specifically, the air gaps 119 are defined by a portion of the surface of lateral side surfaces 121a, 121b of support members 58a, 58b and a portion of the surfaces 76a, 78a, 76b, 78b of electrodes 64a, 66a, 64b, 66b. Air gaps 119 preferably have a width (e.g. shortest distance between an electrode surface and an edge of a tissue grasping surface) greater than about 0.5 mm, and in the range between and including about 0.5 mm to 5.0 mm. More preferably, air gaps 119 preferably have a width greater than about 1 mm, in the range between and including about 1 mm to 3.0 mm.

In the presence of tissue 156 as shown in FIG. 7, the air gaps 119 may be further defined by a portion of the surfaces 166a, 166b of tissue 156. As shown, the portion of the surfaces 166a, 166b of tissue 156 preferably extends between a separation point 123 from electrodes 64a, 66a, 64b, 66b and edges 125a, 125b to grasping surfaces 29a, 29b. Among other things, these three sides help to shape fluid couplings 160 into the triangular shape described below.

Given that air gaps 119 are elongated in that they extend longitudinally along the length of surfaces 62a, 62b and electrodes 64a, 66a, 64b, 66b, the air gaps 119 also provide an open fluid flow channel or trough for fluid 128 from fluid source 130 to flow along the length of surfaces 62a, 62b and electrode surfaces 76a, 78a, 76b, 78b.

As shown in FIG. 6, the outer perimeter edges 125a, 125b to grasping surfaces 62a, 62b of jaws 16a, 16b comprise sharp edges. However, in other embodiments, as shown in FIG. 8, edges 125a, 125b may comprise bevel edges. Edges 125a, 125b preferably comprise beveled edges rather than sharp edges to inhibit inadvertent cutting of tissue 156. However, more importantly, beveled edges are configured to further concentrate a great majority of the electrical power converted to heat in the tissue located in the medial portion of grasping surfaces 62a, 62b. In still other embodiments, as shown in FIG. 16, edges 125a, 125b may comprise a polymer, such as provided by a coating 127, for example, of PTFE while grasping surfaces 62a, 62b comprise a ceramic such as boron nitride.

As shown in FIGS. 3–6, distal end portions 100a, 100b of jaws 16a, 16b preferably comprise a generally domed shape, and provide an obstruction (e.g. the structure forming receptacles 102a, 104a, 102b, 104b for inhibiting fluid 128 from flowing around the distal end 56 of the jaws 16a, 16b and forming a conductive fluid bridge which may form a shunt between certain electrode pairs having different polarities (e.g. 64a, 66a and 64b, 66b).

Similarly to distal end portions 100a, 100b, proximal end portions 114a, 114b of jaws 16a, 16b also provide an obstruction (e.g. the structure forming receptacles 110a, 112a, 110b, 112b) for inhibiting fluid 128 from flowing around the proximal end 54 of the jaws 16a, 16b and forming a conductive fluid bridge which may form a shunt between certain electrode pairs having different polarities (e.g. 64a, 66a and 64b, 66b).

As shown in FIG. 6, base portions 60a, 60b preferably comprise a maximum lateral (width) dimension d equal to or less than the maximum lateral dimension of electrodes 64a, 66a, 64b, 66b. In this manner, the electrical coupling of tissue to electrodes 64a, 66a, 64b, 66b is less likely to be disrupted if tissue contacts base portions 60a, 60b during use of device 10.

Continuing with FIG. 6, preferably the contour of backside surfaces 120a, 120b of jaws 16a, 16b provides one or more obstructions which inhibits fluid 128 from flowing around the backside of the jaws 16a, 16b and forming a conductive fluid bridge which may form a shunt between certain electrode pairs having different polarities (e.g. 64a, 66a and 64b, 66b). As shown, the contour of the backside surfaces 120a, 120b preferably comprises one or more longitudinally extending protrusions 122a, 122b which provide drip edges 124a, 124b for fluid 128 to separate from device 10. If a protrusion 122a, 122b is not utilized (possibly due to size constraints), the contour of the backside surfaces 120a, 120b may comprise one or more longitudinally extending recesses 126a, 126b which also provides drip edges 124a, 124b adjacent thereto for fluid 128 to separate from device 10. In the above manner, conductive fluid 128 flowing medially around the backside of the jaws 16a, 16b is inhibited from forming a bridge across the backside surfaces 120a, 120b of the jaws 16a, 16b and may be redirected to flow along the length of the jaws 16a, 16b, either proximally or distally, until separation therefrom.

As indicated above, device 10 may be used as part of a system. FIG. 9 shows a block diagram of one exemplary embodiment of a system of the invention. As shown in FIG. 9, fluid 128 is provided from a fluid source 130 through a fluid source output fluid line 132 which is acted on by a pump 134 that is connected to input fluid line 44 to electrosurgical device 10.

In a preferred embodiment, the output fluid line 132 and the input fluid line 44 are flexible and are made from a polymer material, such as polyvinylchloride (PVC) or polyolefin (e.g. polypropylene, polyethylene). In another embodiment, the output fluid line 132 and the input fluid line 44 are preferably connected via a male and female mechanical fastener configuration 133, preferably comprising a Luer-Lok® connection from Becton, Dickinson and Company.

Preferably, fluid 128 comprises a saline solution and, more preferably sterile, physiologic saline. It should be understood that where description herein references the use of saline as the fluid 128, other electrically conductive fluids, as well as non-conductive fluids, can be used in accordance with the invention.

For example, in addition to the conductive fluid comprising physiologic saline (also known as "normal" saline, isotonic saline or 0.9 weight-volume percentage sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

In certain embodiments as discussed herein, hypertonic saline, saturated with NaCl to a concentration of about 15% (weight-volume percentage), may be preferred to physiologic saline to reduce the electrical resistivity of the saline from about 50 ohm-cm at 0.9% to about 5 ohm-cm at 15%. This ten-fold reduction in electrical resistivity of the conductive fluid will enhance the reduction in heating (both resistance heating and conduction heating) of tissue and the conductive fluid itself as shown herein.

While a conductive fluid is preferred, as will become more apparent with further reading of this specification, the fluid 128 may also comprise an electrically non-conductive fluid. The use of a non-conductive fluid is less preferred to that of a conductive fluid as the non-conductive fluid does not conduct electricity. However, the use of a non-conductive fluid still provides certain advantages over the use of a dry electrode including, for example, thermal cooling and reduced occurrence of tissue sticking to the electrodes of the device 10. Therefore, it is also within the scope of the invention to include the use of a non-conducting fluid, such as, for example, deionized water or 1.5% glycine.

Returning to FIG. 9, energy to heat tissue is provided from an energy source, such as an electrical generator 136 which may provide alternating current, RF electrical energy at various rates (i.e. power) to electrodes 64a, 66a, 64b, 66b. As to the frequency of the RF electrical energy, it is preferably provided within a frequency band (i.e. a continuous range of frequencies extending between two limiting frequencies) in the range between and including about 9 kHz (kilohertz) to 300 GHz (gigahertz). More preferably, the RF energy is provided within a frequency band in the range between and including about 50 kHz (kilohertz) to 50 MHz (megahertz). Even more preferably, the RF energy is provided within a frequency band in the range between and including about 200 kHz (kilohertz) to 2 MHz (megahertz). Most preferably, RF energy is provided within a frequency band in the range between and including about 400 kHz (kilohertz) to 600 kHz (kilohertz).

As shown, the system may be configured to first direct the RF power from the generator 136 via a cable 138 to a power measurement device 140 that measures the actual RF power provided from the generator 136. In one exemplary embodiment, preferably the power measurement device 140 does not turn the RF power off or on, or alter the RF power in any way. Rather, a power switch 142 connected to the generator 136 is preferably provided by the generator manufacturer and is used to turn the generator 136 on and off.

The power switch 142 can comprise any switch to turn the power on and off, and is commonly provided in the form of a footswitch or other easily operated switch, such as a switch 142a mounted on the electrosurgical device 10. The power switch 142 or 142a may also function as a manually activated device for increasing or decreasing the rate of energy provided from the surgical device 10. Alternatively, internal circuitry and other components of the generator 136 may be used for automatically increasing or decreasing the rate of energy provided to the surgical device 10.

As shown in FIG. 9, in series after power measurement device 140, cable 34 of device 10 is connected to power measurement device 140 to provide the RF power from generator 136 to the device 10. Alternatively, in other embodiments, power measurement device 140 may be eliminated and cable 34 may be connected directly to generator 136.

Power P is preferably measured before it reaches the electrosurgical device 10. For the situation where capacitive and inductive effects are negligibly small, from Ohm's law, power P, or the rate of energy delivery (e.g. joules/sec), may be expressed by the product of current times voltage (i.e. I×V), the current squared times resistance (i.e. $I^2×R$), or the voltage squared divided by the resistance (i.e. $V^2/R$); where the current I may be measured in amperes, the voltage V may be measured in volts, the electrical resistance R may be measured in ohms, and the power P may be measured in watts (joules/sec). Given that power P is a function of current I, voltage V, and resistance (impedance) R as indicated above, it should be understood, that a change in power P is reflective of a change in at least one of the input variables. Thus, one may alternatively measure changes in such input variables themselves, rather than power P directly, with such changes in the input variables mathematically corresponding to a changes in power P as indicated above. Furthermore, it should be understood that the terms "impedance" and "resistance" as used herein are used interchangeably given the capacitive and inductive effects are considered negligible.

Heating of the tissue is preferably performed by means of electrical resistance heating. In other words, increasing the temperature of the tissue as a result of electric current flow through the tissue, with the associated electrical energy being converted into thermal energy (i.e. heat) via accelerated movement of ions as a function of the tissue's electrical resistance. Resistance heating provides direct, instantaneous heating inside tissue due to the current flow through the tissue.

Heating of the tissue is also accomplished by thermal conduction heating. With conduction, tissue is heated by thermal energy flowing through tissue to adjacent tissue by virtue of gradients in temperature. The source of the conduction heating is ultimately from the resistance heating.

Once a steady-state condition has been achieved, and all temperatures everywhere in the vicinity of the electrodes and grasped tissue are not changing with time, it is a reasonable approximation to assume that all heat delivered to tissue by RF power is ultimately carried away by the convective cooling of the flowing fluid 128. Thus, the flow of the fluid 128 not only physically surrounds the grasped tissue, but it also can be seen as a cooling blanket around the targeted tissue treatment site and also limits the maximum temperature of the fluid 128 heated by tissue by forcing the heated fluid to drip off the electrodes and jaws of the device as the fluid 128 is replenished.

In one exemplary embodiment, the system may comprise a flow rate controller 144. Preferably, the flow rate controller 144 is configured to actively link and mathematically relate the power P and the flow rate Q of fluid 128 to one another. Preferably, the controller 144 receives an input related to the level of RF power being provided from the generator 136 (e.g. from power measurement device 140), and adjusts the flow rate Q of the fluid 128 to device 10, thereby adjusting the temperature (preferably within a predetermined range) of tissue, particularly outside the targeted tissue treatment site (i.e. outside surfaces 62a, 62b).

In one embodiment, the flow rate controller 144 may receive an input signal 146 (e.g. from the power measurement device 140) and calculate an appropriate mathematically predetermined fluid flow rate Q to achieve a predetermined tissue and/or fluid temperature. The flow rate controller may include a selection switch 148 that can be set to provide a safety factor (e.g. 10%, 20%, 30%) beyond the mathematically predetermined fluid flow rate Q. An output signal 150 from the flow rate controller 144 may then be sent to the pump 134 which is correlated to the predetermined flow rate Q of fluid 128, and thereby provide an appropriate fluid flow rate Q which corresponds to the power P being provided by the generator 136.

In another exemplary embodiment, elements of the system are physically included together in one electronic enclosure. One such embodiment is shown by enclosure within the outline box 152 of FIG. 9. In the illustrated embodiment, the pump 134, flow rate controller 144, and power measurement device 140 are enclosed within an enclosure, and these elements are connected through electrical connections to allow signal 146 to pass from the power measurement device 140 to the flow rate controller 144, and signal 150 to pass from the flow rate controller 144 to the pump 134. Other elements of a system can also be included within one enclosure, depending upon such factors as the desired application of the system, and the requirements of the user.

In various embodiments, the flow rate controller 144 of FIG. 9 can be a simple "hard-wired" analog or digital device that requires no programming by the user or the manufacturer. The flow rate controller 144 can alternatively include a processor, with or without a storage medium, in which the flow rate Q of fluid 128 is performed by software, hardware, or a combination thereof. In another embodiment, the flow rate controller 144 can include semi-programmable hardware configured, for example, using a hardware descriptive language, such as Verilog. In another embodiment, the flow rate controller 144 of FIG. 9 is a computer, microprocessor-driven controller with software embedded.

In yet another embodiment, the flow rate controller 144 can include additional features, such as a delay mechanism, such as a timer, to automatically keep the flow of fluid 128 on for several seconds after the RF power is turned off to provide a post-coagulation cooling of the tissue or "quench," which can increase the strength of the tissue seal. Also, in another embodiment, the flow rate controller 144 can include a delay mechanism, such as a timer, to automatically turn on the flow of fluid 128 several seconds before the RF power is turned on to inhibit the possibility of undesirable effects as sticking, desiccation, smoke production and char formation.

In still another embodiment, the flow rate controller 144 can be used to turn the flow on and off in response to an electrical switch, such as 142a, located in the handle 22. This would automatically turn the flow on when the jaws were clamped on tissue, and turn the flow off when the jaws were unclamped from tissue. As the lever 24 is moved toward the grip 26 of the handle 22, a normally-closed single pole, single-throw electrical switch (e.g. switch 142a) could be activated, completing a circuit, either through the power measurement device 140 or an additional pair of wires that would exit the handle 22 of device 10 and continue directly to the controller 144. Such a switch would function in a manner similar to that of the generator footswitch to turn the RF power on and off.

Instead of using an electrical switch as described above, a separate on-off flow switch 143 could be located in the handle 22 such that it would be normally closed when the device jaws were open, and little or no fluid 128 could flow from, for example a fluid source such as a passive gravityfed saline delivery system. As lever 24 is moved into a latched or use position, clamping the jaws on tissue in a use position, a simple mechanism (push-rod, cam, lever) would open the flow switch 143 and allow fluid 128 to flow. This would be one of the simplest forms of flow control, and would be useful to minimize wasteful dripping of fluid 128 when the device 10 is not being used, as well as to minimize the amount of fluid 128 that would have to be suctioned out of the patient at a later time.

Also in another embodiment, the flow rate controller 144 can include a low level flow standby mechanism, such as a valve, which continues the flow of fluid 128 at a standby flow level (which prevents the flow rate from going to zero when the RF power is turned off) below the surgical flow level ordinarily encountered during use of device 10.

The pump 134 can be any suitable pump used in surgical procedures to provide saline or other fluid 128 at a desired flow rate Q. Preferably, the pump 134 comprises a peristaltic pump. With a rotary peristaltic pump, typically fluid 128 is conveyed within the confines of fluid line 132 by waves of contraction placed externally on the line which are produced mechanically, typically by rotating rollers which squeeze flexible tubing against a support intermittently. Alternatively, with a linear peristaltic pump, typically a fluid 128 is conveyed within the confines of a flexible tube by waves of contraction placed externally on the tube which are produced mechanically, typically by a series of compression fingers or pads which squeeze the flexible tubing against a support sequentially. Peristaltic pumps are generally preferred for use as the electromechanical force mechanism (e.g. rollers driven by electric motor) does not make contact the fluid 128, thus reducing the likelihood of inadvertent contamination.

Alternatively, pump 134 can be a "syringe pump", with a built-in fluid supply. With such a pump, typically a filled syringe is located on an electromechanical force mechanism (e.g. ram driven by electric motor) which acts on the plunger of the syringe to force delivery of the fluid 128 contained therein. Alternatively, the syringe pump may comprise a double-acting syringe pump with two syringes such that they can draw saline from a reservoir (e.g. of fluid source 130), either simultaneously or intermittently. With a double acting syringe pump, the pumping mechanism is generally capable of both infusion and withdrawal. Typically, while fluid 128 is being expelled from one syringe, the other syringe is receiving fluid 128 therein from a separate reservoir. In this manner, the delivery of fluid 128 remains continuous and uninterrupted as the syringes function in series. Alternatively, it should be understood that a multiple syringe pump with two syringes, or any number of syringes, may be used in accordance with the invention.

In various embodiments, fluid 128, such as conductive fluid, can also be provided from an intravenous (IV) bag full of saline (e.g. of fluid source 130) that flows under the force of gravity. In such a manner, the fluid 128 may flow directly to device 10, or first to the pump 134 located there between. In other embodiments, fluid 128 from a fluid source 130, such as an IV bag, can be provided through a flow rate controller 144 which directly acts on controlling the flow of fluid 128, rather than indirectly by means of pump 134. Such a flow rate controller 144 may provide a predetermined flow rate Q by adjusting the cross sectional area of a flow orifice (e.g. lumen of fluid line such as 44 or 132) while also sensing the flow rate Q with a sensor such as an optical drop counter. Furthermore, fluid 128 from a fluid source 130, such as an IV bag, an be provided through automatically or manually adjusting flow rate controller 144, such as a roller clamp (which also adjusts the cross sectional area of a flow orifice such as lumen of fluid line 44 or 132) and is adjusted manually by, for example, the user of device 10 in response to their visual observation that the fluid rate Q needs adjustment.

Similar pumps can be used in connection with the invention, and the illustrated embodiments are exemplary only. The precise configuration of the pump 134 is not critical to the invention. For example, pump 134 may include other types of infusion and withdrawal pumps. Furthermore, pump 134 may comprise pumps which may be categorized as piston pumps, rotary vane pumps (e.g. axial impeller, centrifugal impeller), cartridge pumps and diaphragm pumps. In some embodiments, the pump 134 can be substituted with any type of flow controller, such as a manual roller clamp used in conjunction with an IV bag, or combined with the flow controller to allow the user to control the flow rate of conductive fluid to the device. Alternatively, a valve configuration can be substituted for pump 134.

In various embodiments, other configurations of the system can be used with device 10, and the illustrated embodiments are exemplary only. For example, the fluid source 130, pump 134, generator 136, power measurement device 140 or flow rate controller 144, or any other components of the system not expressly recited above, may comprise a portion of the device 10. For example, in one exemplary embodiment the fluid source 130 may comprise a compartment of the device 10 which contains fluid 128, as indicated at reference character 130a. In another exemplary embodiment, the compartment may be detachably connected to device 10, such as a canister which may be attached via threaded engagement with the device 10. In yet another exemplary embodiment, the compartment may be configured to hold a pre-filled cartridge of fluid 128, rather than the fluid directly.

Also for example, with regards to alternatives for the generator 136, an energy source, such as a direct current (DC) battery used in conjunction with inverter circuitry and a transformer to produce alternating current at a particular frequency, may comprise a portion of device 10, as indicated at reference character 136a. In one embodiment the battery element of the energy source may comprise a rechargeable battery. In yet another exemplary embodiment, the battery element may be detachably connected to device 10, such as for recharging.

Turning to FIG. 7, upon being connected to generator 136 and fluid source 130, fluid 128 is expelled from side flow passage fluid exit openings 96a, 98a, 96b, 98b. Fluid 128 expelled from the side flow passage fluid exit openings 96a, 98a, 96b, 98b preferably forms a thin film coating on surfaces 76a, 78a, 76b, 78b of electrodes 64a, 66a, 64b, 66b. Excess fluid 128 may flow partially around to the backside surfaces 120a, 120b and form a droplet 154 which subsequently falls and separates from device 10, preferably from drip edges 124a, 124b. Fluid 128 preferably is inhibited from locating on surfaces 62a, 62b as already described herein.

As shown in FIG. 7, when device 10 is introduced to tissue 156, typically a surgeon will grasp a small amount of tissue 156, shown here as a vessel with a lumen 158, and compress the tissue 156 between the grasping surfaces 62a, 62b of the jaws 16a, 16b. Where the tissue includes a lumen 158, such as the lumen of a blood vessel, the lumen will generally become occluded. Substantially simultaneously with the surgeon's manipulation of the tissue 156, fluid 128 is continuously being expelled from the side flow passage fluid exit openings 96a, 98a, 96b, 98b.

Fluid 128 expelled from the side flow passage flow exit openings 96a, 98a, 96b, 98b couples tissue 156 and electrodes 64a, 66a, 64b, 66b. As shown in FIG. 7, fluid couplings 160, 162, 164 comprise discrete, localized webs, and more specifically triangular shaped webs. Fluid couplings 160, 162, 164 provide localized wells of fluid 128 which enhance the electrical coupling of tissue 156 and electrodes 64a, 66a, 64b, 66b and remove heat generated in tissue 156 by convection. Furthermore, as discussed in greater detail below, couplings 160, 162, 164 provide a diversion there through for at least a portion of the electrical current flowing in tissue 156 outside grasping surfaces 62a, 62b, whereby the amount of electrical energy available to be converted into heat in tissue 156 outside grasping surfaces 62a, 62b may be correspondingly reduced. Additionally, couplings 160, 162, 164 provide a lubricant which lubricates the interface between surfaces 76a, 78a, 76b, 78b of electrodes 64a, 66a, 64b, 66b and surfaces 166a, 166b of tissue 156 which inhibits sticking between electrodes 64a, 66a, 64b, 66b and tissue 156 electrically coupled therewith.

Continuing with FIG. 7, as shown the fluid couplings 160, 162, 164 are laterally outside grasping surfaces 62a, 62b of the jaws 16a, 16b. Turning to fluid couplings 160 specifically, as shown they are laterally positioned between a portion of surfaces 76a, 78a, 76b, 78b of electrodes 64a, 66a, 64b, 66b and grasping surfaces 62a, 62b of the jaws 16a, 16b along outer perimeter edges 125a, 125b. Given their location, in addition to the benefits of electrical coupling, fluid couplings 160 remove heat from and cool the portion of tissue 156 laterally adjacent grasping surfaces 62a, 62b and also cool support members 58a, 58b along side surfaces 121a, 121b thereof.

As shown in FIG. 7, in order to provide fluid 128 at fluid couplings 160, preferably a portion of the flow of fluid 128 is provided from certain of the side fluid flow passages 92a, 94a, 92b, 94b configured to direct fluid 128 to that portion of tissue 156 that is laterally adjacent grasping surfaces 62a, 62b.

Turning fluid couplings 162, as shown in FIG. 7, they are positioned laterally relative to surfaces 76a, 78a, 76b, 78b of electrodes 64a, 66a, 64b, 66b. Given their location, in addition to the benefits of electrical coupling, fluid couplings 162 remove heat and cool the portion of tissue 156 laterally adjacent electrodes 64a, 66a, 64b, 66b. As shown in FIG. 7, in order to provide fluid 128 at fluid couplings 162, preferably a portion of the flow of fluid 128 is provided from certain of the side fluid flow passages 92a, 94a, 92b, 94b configured to direct fluid 128 to that portion of tissue 156 that is laterally adjacent electrodes 64a, 66a, 64b, 66b.

Turning to fluid couplings 164, unlike fluid couplings 160 and 162, fluid couplings 164 are not configured to cool tissue 156. Rather, fluid couplings 164 are configured to remove heat and cool support members 58a, 58b and base portions 60a, 60b of jaws 16a, 16b. As shown in FIG. 7, in order to provide fluid 128 at fluid couplings 164, preferably a portion of the flow of fluid 128 is provided from certain of the side fluid flow passages 92a, 94a, 92b, 94b configured to direct fluid 128 to support members 58a, 58b and base portions 60a, 60b of jaws 16a, 16b.

Surfaces 166a, 166b of tissue 156 are often uneven or undulated with microscopic peaks and valleys. Without fluid 128, the area of electrical coupling of tissue 156 to the surfaces 76a, 78a, 76b, 78b of electrodes 64a, 66a, 64b, 66b can be limited to the isolated peaks in the tissue surfaces 166a, 166b. In this situation, upon the application of RF energy to tissue 156, the electrical coupling area of surfaces 166a, 166b, by virtue of being limited to the tissue peaks, results in corresponding increase in current density through the peaks which has the ability to desiccate and char the tissue 156. Conversely, fluid 128 enters and occupies the previously unoccupied valleys and gaps 167 (as shown in FIG. 8) between tissue surfaces 166a, 166b and the surfaces 76a, 78a, 76b, 78b of electrodes 64a, 66a, 64b, 66b and enhances the electrical coupling of the tissue surfaces 166a, 166b to the surfaces 76a, 78a, 76b, 78b of electrodes 64a, 66a, 64b, 66b.

Furthermore, the intimacy of electrical coupling between surfaces 166a, 166b of tissue 156 and the surfaces 76a, 78a, 76b, 78b of electrodes 64a, 66a, 64b, 66b often decreases as the tissue shrinks away from surfaces 76a, 78a, 76b, 78b and/or desiccates during tissue treatment. Conversely, fluid 128 provides a mechanism to offset losses in electrical coupling due to tissue shrinkage and/or desiccation by entering and occupying any gaps 167 (as shown in FIG. 8) which have developed between surfaces 166a, 166b of tissue 156 and the surfaces 76a, 78a, 76b, 78b of electrodes 64a, 66a, 64b, 66b during treatment.

Once the jaws 16a, 16b are closed to a use position, RF power is then provided to the tissue 156. RF power is provided at the tissue surface 166a, 166b and below the tissue surface 166a, 166b into the tissue 156 directly from electrodes 64a, 66a, 64b, 66b, as well as through the fluid couplings 160 and 162 to a targeted tissue treatment site, here between grasping surfaces 62a, 62b, thereby heating the tissue 156 to coagulate, shrink, weld or otherwise treat the tissue 156.

If desired, after treating the tissue 156 between the jaws 16a, 16b, the jaws 16a, 16b can be held clamped together and cutting mechanism 32 can be actuated to cut the tissue 156. As shown in FIG. 5, cutting mechanism 32 preferably comprises a cutting blade with a sharpened distal end. Preferably cutting mechanism 32 is actuated by rotating paddles 30 distally to longitudinally extend the blade distally and thereafter rotating the paddles 30 proximally to longitudinally retract the cutting blade proximally.

In order to reduce tissue treatment time, lateral thermal spread and ensuing necrosis of tissue 156 laterally outside grasping surfaces 62a, 62b, particularly tissue 156 laterally adjacent grasping surfaces 62a, 62b, adjacent the electrodes 64a, 66a, 64b, 66b and there in between, it is desirable to concentrate the energy to the tissue 156 between grasping surfaces 62a, 62b of device 10 as shown below as part of the present invention. Before continuing, however, it should be noted that the examples below should only be considered to an order of magnitude approximation for explanatory purposes.

Electrical resistance Re to the passage of RF current can be described by equation (1) below:

$$R_e = \rho_e L / A \qquad (1)$$

where:
  $R_e$=electrical resistance (ohms);
  $\rho_e$=electrical resistivity (ohm-cm);
  L=length (cm); and
  A=area (cm$^2$).

In determining the electrical resistance of tissue $R_{et}$ located between surfaces 62a, 62b of device 10, the length of tissue L is represented by the width across surfaces 62a, 62b of jaws 16a, 16b. The area A of the tissue is represented by a longitudinal dimension of surfaces 62a, 62b and the thickness of tissue between surfaces 62a, 62b. In other words, with reference to FIGS. 5 and 10 for dimensions a, b and c, the electrical resistance of tissue $R_{et}$ located between surfaces 62a, 62b using equation (1) is expressed as:

$$R_{et\ (between\ grasping\ surfaces)} = \rho_{et} b/ac \quad (2)$$

By way of example, where the tissue 156 located between surfaces 62a, 62b of device 10 has a dimension a of 0.025 cm, a dimension b of 0.3 cm, a dimension c of 3 cm and an electrical resistivity of the tissue $\rho_{et}$ of 200 ohm-cm before treatment, the electrical resistance of the tissue $R_{et}$ between surfaces 62a, 62b of device 10 is about 800 ohms.

Conversely, for tissue 156 adjacent electrodes 64a, 66a, 64b, 66b, equation (1) is expressed as:

$$R_{et\ (adjacent\ the\ electrodes)} = \rho_{et} a/bc \quad (3)$$

Note that the area A of tissue 156 is now measured by the product of (b)(c). For tissue 156 adjacent electrodes 64a, 66a, 64b, 66b, dimension b comprises the portion of the circumference of the electrodes 64a, 66a, 64b, 66b electrically coupled to tissue 156. Thus, as shown in FIG. 10, dimension b can be approximated by about one-quarter of the circumference of electrodes 64a, 66a, 64b, 66b. Consequently, where the diameter of electrodes 64a, 66a, 64b, 66b is 0.15 cm, dimension b is about 0.1 cm for each electrode. Next, when dimension C is held constant (i.e. 3 cm), area A for each electrode 64a, 66a, 64b, 66b is about 0.3 cm².

In the case of four electrodes with the electrical potential and positioning such as electrodes 64a, 64b and 66a, 66b, the electrical resistance of the tissue $R_{et}$ adjacent electrodes 64a, 64b and 66a, 66b could be considered in parallel. However, in order to assume a worse case scenario, as well as simply the system, the existence of only two electrodes (e.g. 64a, 66b) will be assumed in continuing with the calculations herein.

Turning to dimension a, as shown in FIG. 10 electrodes 64a, 66b are recessed relative to surfaces 62a, 62b. Dimension a relative to electrodes 64a, 66b can be somewhat arbitrarily estimated as being about twice dimension a between surfaces 62a, 62b. Thus, using a dimension a of 0.05 cm, and keeping the electrical resistivity of the tissue Pet constant at 200 ohm-cm, the electrical resistance of the tissue $R_{et}$ adjacent the electrodes 64a, 66b is about 33 ohms. Thus, the above illustrates that the electrical resistance of the tissue $R_{et}$ adjacent electrodes 64a, 66b can be substantially lower than the electrical resistance of the tissue $R_{et}$ between surfaces 62a, 62b.

The total electrical resistance $R_{eTotal}$ encountered in an electrical circuit for resistors in series can be approximated by adding the electrical resistance of each resistor in the circuit. Thus, for the example above, the total electrical resistance $R_{eTotal}$ may be approximated as 866 ohms. Continuing with the above, assuming a power P of 35 watts and a total electrical resistance $R_{eTotal}$ is 866 ohms, from Ohm's Law the current I is about 0.2 amps. In turn, also from Ohm's Law. the amount of the power P converted to heat in the tissue 156 located between surfaces 62a, 62b of device 10 is about 32 watts while the power P converted into heat in the tissue 156 adjacent electrodes 64a, 66b is about 3 watts. Stated another way, about 90% of the power is converted to heat in the resistance of the tissue 156 located between surfaces 62a, 62b of device 10.

Once the current I flowing through tissue 156 is known, the current density in tissue 156 may also be calculated. Current density is a vector quantity whose magnitude is the ratio of the magnitude of current I flowing through a substance to the cross-sectional area A perpendicular to the current direction of flow and whose direction points in the direction of the current flow. Current density is commonly expressed in amperes per square centimeter (i.e. amps/cm²).

In light of the above definition, the current density in tissue 156 between surfaces 62a, 62b of device 10 when using an area A of 0.075 cm² (i.e. dimension a of 0.025 cm and dimension c of 3 cm) as above is about 2.7 amps/cm². Conversely, the current density in tissue 156 adjacent electrodes 64a, 66b when using an area A of 0.3 cm² as above is about 0.6 amps/cm². Thus, the current density in tissue 156 between surfaces 62a, 62b of device 10 is on a magnitude of 4 times greater than the current density in tissue 156 adjacent electrodes 64a, 66a, 64b, 66b for the preceding example.

Figure 11:
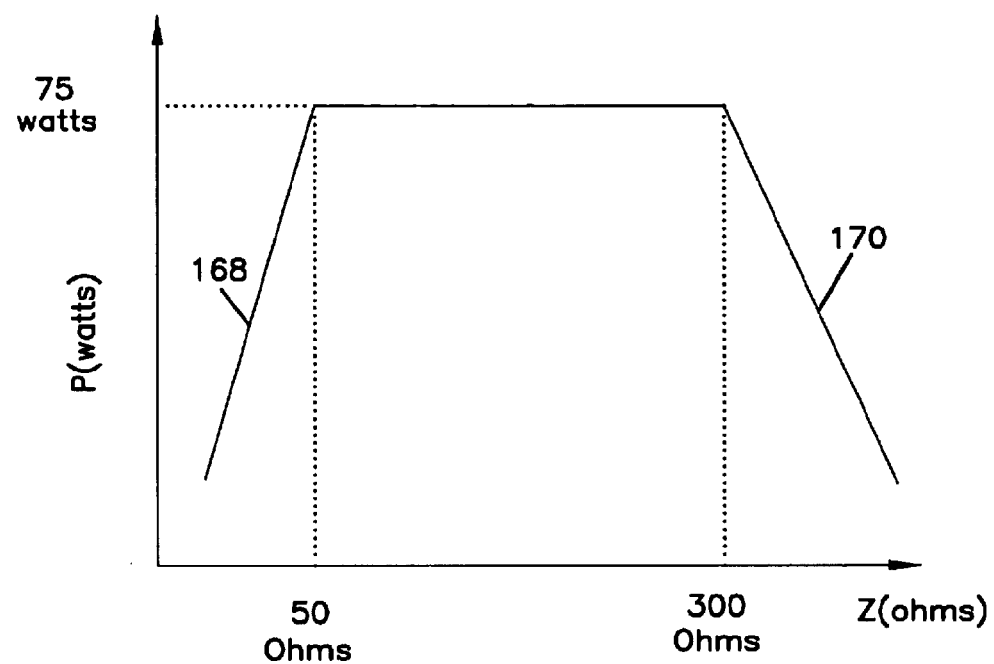
FIG. 11 is an exemplary graph that describes the relationship of load impedance (Z, in ohms) and generator output power (P, in watts), for an exemplary generator output of 75 watts in a bipolar mode.

In certain instances, use of device 10 may result in a load impedance outside the working range of a general-purpose generator 136. For example, the schematic graph of FIG. 11 shows the general output curve of a typical general-purpose generator, with the output power changing as load (tissue plus cables) impedance Z changes. Load impedance Z (in ohms) is represented on the X-axis, and generator output power P (in watts) is represented on the Y-axis. In the illustrated embodiment, the electrosurgical power (RF) is set to 75 watts in a bipolar mode.

As shown in FIG. 11, the power P will remain constant as it was set as long as the impedance Z stays between two cut-offs, low and high, of impedance, that is, for example, between 50 ohms and 300 ohms in the illustrated embodiment. Below load impedance Z of 50 ohms, the power P will decrease, as shown by the low impedance ramp 168. Above load impedance Z of 300 ohms, the power P will decrease, as shown by the high impedance ramp 170. This change in output is invisible to the user of the generator and not evident when the generator is in use, such as in an operating room.

As shown by the exemplary calculations above, the high impedance cut-off where power P begins to decrease as shown by high impedance ramp 170 may be exceeded with use of device 10 and quite possibly be completely outside the working range of generator 136. Consequently, as shown in FIG. 9, it may be necessary to provide an impedance transformer 172 in a series circuit configuration between electrodes 64a, 66a, 64b, 66b of device 10 and the power output of generator 136. Consequently, the impedance transformer 172 may be provided with device 10, the generator 136 or any of the wire connectors (e.g. cable 34) connecting device 10 and generator 136. Impedance transformer 172 is configured to match the load impedance provided to generator 136 such that it is within the working range of the generator 136 and, more preferably in the working range between the low and high cut-offs.

As already described herein, an exemplary electrical resistivity of the tissue Pet is about 200 ohm-cm. Also as already described herein, for saline the electrical resistivity of the fluid $\rho_{ef}$ is about 50 ohm-cm for physiologic saline and about 5 ohm-cm for hypertonic saline. Thus, the electrical resistivity of the tissue Pet for the present example is about four times to forty times greater than the electrical resistivity of the fluid $\rho_{ef}$. Consequently, assuming all else equal, electrical current I will flow more predominately through the conductive fluid 24 rather than through tissue 32. The position of fluid couplings 160 is configured for this and exploits it.

As electrical current flows in the tissue 156 between surfaces 62a, 62b and exits from between surfaces 62a, 62b, it will seek a path to the counter electrode comprising the least electrical resistance $R_e$. As already discussed herein, among other things, electrical resistance $R_e$ is a function of electrical resistivity $\rho_e$ and length L of the resistor. In the case of physiologic saline, the electrical resistivity of the conductive fluid $\rho_{ef}$ making up fluid couplings 160 is one-fourth the electrical resistivity of the tissue $\rho_{et}$. Furthermore, as shown in FIG. 7, the shortest distance for the electrical current I to travel to the counter electrode upon exiting from between surfaces 62a, 62b is through fluid couplings 160. An exemplary distance between the edges 125a, 126b to surfaces 62a, 62b and the closest portion of an electrode surface 76a, 76b, 78a, 78b thereto is in the range between and including about 0.5 mm to 5.0 mm. More preferably, the distance between the edges 125a, 126b to surfaces 62a, 62b and the closest portion of an electrode surface 76a, 76b, 78a, 78b is in the range between and including about 1 mm to 3.0 mm.

Consequently, electrosurgical device 10 and the system is configured to provide a diversion for (and preferably divert at least a portion of) electrical current, upon exiting from between grasping surfaces 62a, 62b, to flow at least partially through conductive fluid 128 before reaching the counter electrode. In other words, couplings 160 and 162 provide a diversion there through for at least a portion of the electrical current flowing in tissue 156 outside grasping surfaces 62a, 62b, whereby the amount of electrical energy available to be converted into heat in tissue 156 outside grasping surfaces 62a, 62b may be correspondingly reduced.

Similar to the counter electrode side of the electrical path, as electrical current flows from the source electrodes and enters between surfaces 62a, 62b it will also seek a path to the counter electrode comprising the least electrical resistance $R_e$. Consequently, in addition to the above, device 10 and the system are also configured to provide a diversion for (and preferably divert at least a portion of) at least a portion of the electrical current, upon leaving the source electrode, at least partially through conductive fluid 128 before entering between grasping surfaces 62a, 62b.

Figure 12:
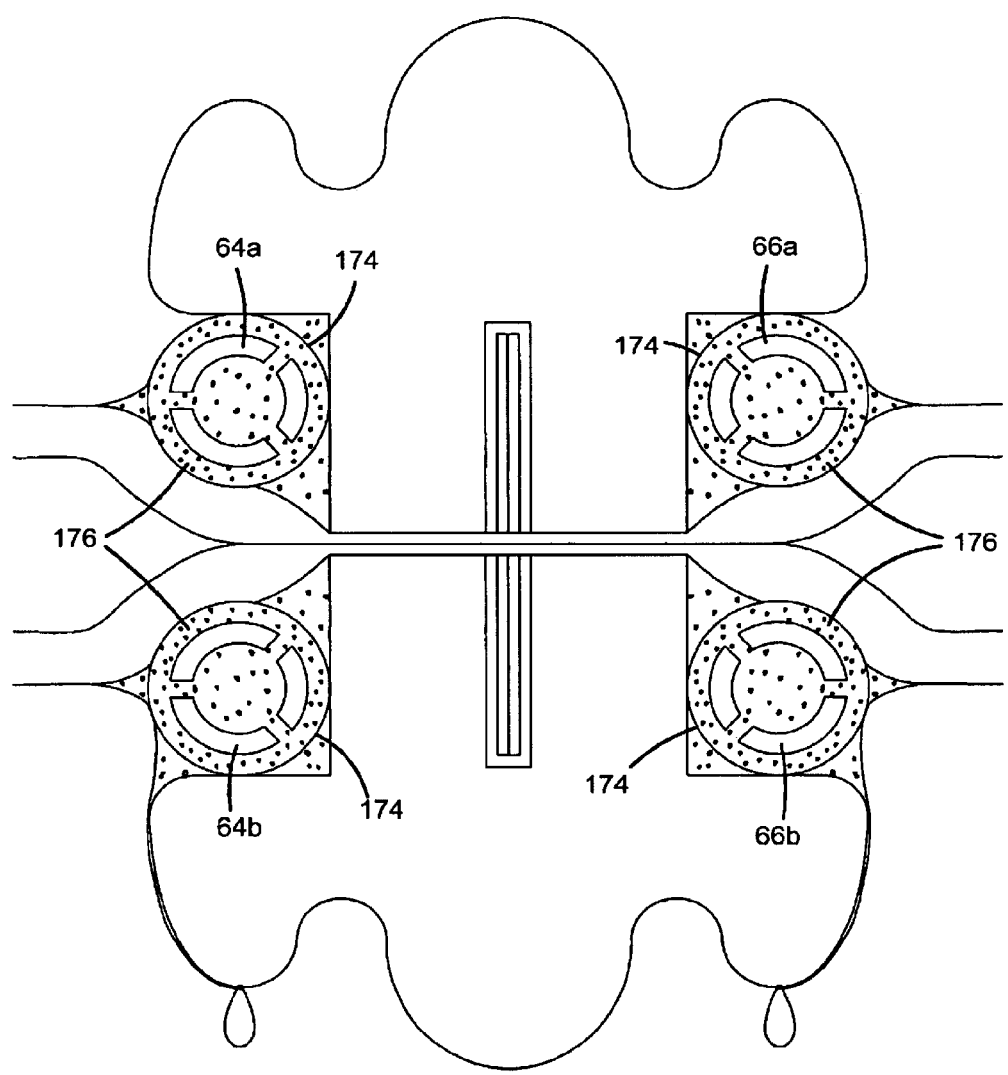
FIG. 12 is a cross-sectional view of another alternative embodiment of jaws 16a, 16b of the device of FIG. 1 taken along line 5—5 of FIG. 5.
Figure 13:
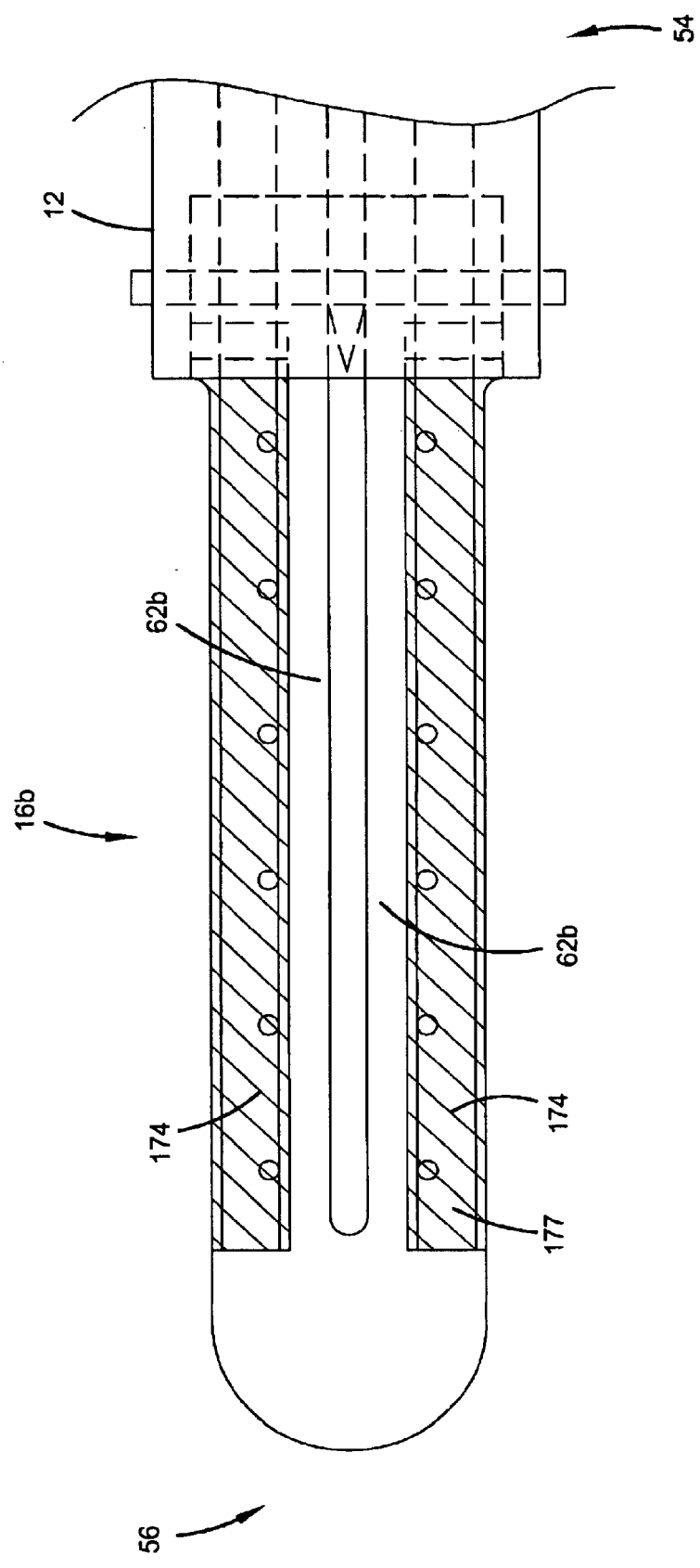
FIG. 13 is a close-up top view of the alternative embodiment of jaws 16a, 16b of FIG. 12 with jaw 16a removed.

In light of the above, it may be desirable to increase the size (i.e. volume and area) of the fluid coupling between tissue 156 and the electrodes 64a, 66a, 64b, 66b. More specifically, preferably the jaws 16a, 16b are configured such that tissue 156 is inhibited from direct contact with the electrodes 64a, 66a, 64b, 66b. Referring to FIGS. 12 and 13, a stand-off 174, here a separator which holds two bodies separate from one another preferably at a predetermined distance, inhibits the tissue 156 from direct contact with surfaces 76a, 78a, 76b, 78b of electrodes 64a, 66a, 64b, 66b.

As shown, stand-off 174 preferably comprises a coil, preferably comprising electrically insulated surfaces, superimposed (overlying) and wrapped around the electrode surfaces 76a, 78a, 76b, 78b, thus providing a helical flow channel 177 between bordering windings of the coil. As a result, fluid couplings 160 and 162 merge in a new fluid coupling shown at 176. Fluid coupling 176, by virtue of its increased size, provides an even greater diversion than fluid coupling 160 for at least a portion of the electrical current flowing in tissue 156 outside grasping surfaces 62a, 62b and, consequently, further reduces the amount of electrical energy available to be converted into heat in tissue 156 outside grasping surfaces 62a, 62b.

Preferably the electrically insulative surfaces of the coil are provided by the coil being formed of an electrically insulative material, such as a polymer. For assembly, preferably each electrode 64a, 66a, 64b, 66b is passed through the center longitudinal aperture of a coil, with the coil wrapped around and extending along the length of the surfaces 76a, 78a, 76b, 78b of electrodes 64a, 66a, 64b, 66b between the distal and proximal connector portions of jaws 16a, 16b which connect the electrodes 64a, 66a, 64b, 66b to the jaws 16a, 16b.

Figure 14:
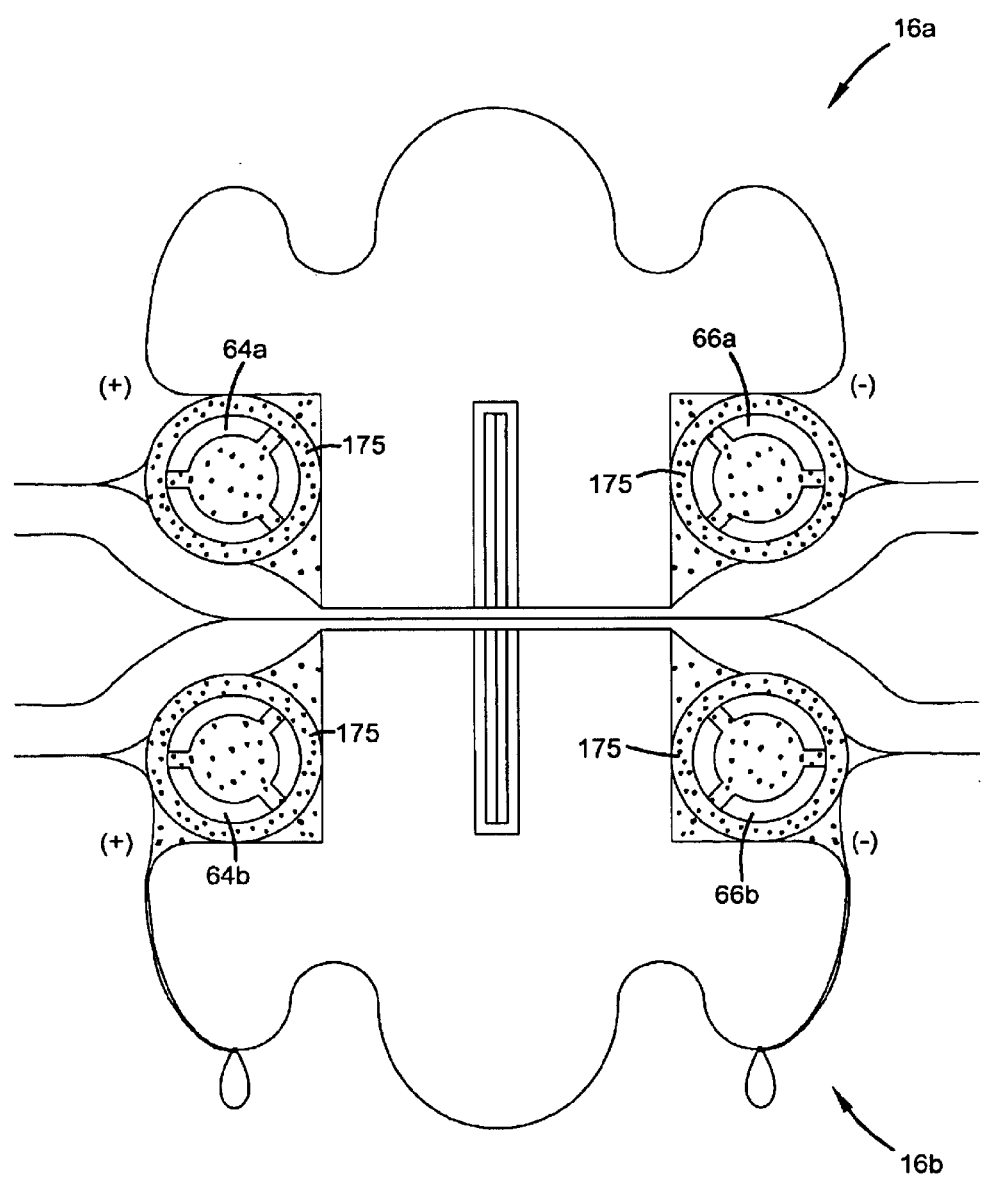
FIG. 14 is a cross-sectional view of another alternative embodiment of jaws 16a, 16b of the device of FIG. 1 taken along line 5—5 of FIG. 5.

In yet another embodiment, the stand-off may comprise a material pervious to the passage of fluid 128 therethrough. As shown in FIG. 14, stand-off 175 may comprise a porous structure which includes a plurality of tortuous and interconnected fluid flow passages which provide and distribute fluid 128 to tissue 156.

Similar to stand-off 174, preferably stand-off 175 comprises a electrically insulative material, such as a polymer or ceramic, superimposed over the electrode surfaces 76a, 78a, 76b, 78b. With an electrically insulative porous structure, RF energy is provided to tissue 156 through the electrically conductive fluid 128 contained within the plurality of interconnected tortuous pathways rather than the porous material itself. A porous polymer structure may be provided by a cellular solid comprising interconnected voids which define the tortuous and interconnected passages. For example, the porous polymer structure may comprise a polymer foam at least partially comprising an open cellular structure. Furthermore, in certain embodiments, the stand-off 175 may comprise a compressible, resilient structure, such as provided by a flexible or semi-rigid polymer foam. In this manner, the stand-off 175 can deform around tissue 156 to provide better electrical and fluid coupling therewith.

In certain embodiments, the electrodes 64a, 66a, 64b, 66b may also comprise a material pervious to the passage of fluid 128 therethrough, such as a porous metal. The discrete, linear side flow passages 92a, 94a, 92b, 94b may be either supplemented with or replaced by a plurality of tortuous, interconnected pathways formed in the porous material which, among other things, provide porous electrode surfaces 76a, 78a, 76b, 78b which more evenly distribute fluid flow and provide fluid 128 to tissue 156.

Preferably the porous materials provide for the wicking (i.e. drawing in of fluid by capillary action or capillarity) of the fluid 128 into the pores of the porous material. In order to promote wicking of the fluid 128 into the pores of the porous material, preferably the porous material, and in particular the surface of the tortuous pathways, is hydrophilic. The porous material may be hydrophilic with or without post treating (e.g. plasma surface treatment such as hypercleaning, etching or micro-roughening, plasma surface modification of the molecular structure, surface chemical activation or crosslinking), or made hydrophilic by a coating provided thereto, such as a surfactant.

As described herein, in order that heat may be transferred away from surfaces 62a, 62b during use of device 10, preferably the material for support members 58a, 58b (particularly the medial portion of support members 58a, 58b adjacent surfaces 62a, 62b) and base portions 60a, 60b have a high thermal conductivity. As shown above, given that the vast amount of the power provided to tissue 156 is converted to heat in the tissue 156 between surfaces 62a, 62b of device 10, it may be necessary to configure support members 58a, 58b and bases 60a, 60b such that surfaces 62a, 62b do not overheat. However, support members 58a, 58b and bases 60a, 60b should be also configured such that surfaces 62a, 62b do not overcool. Preferably, during a typical use of device 10, surfaces 62a, 62b should remain in the temperature range between and including about 75° C. to 120° C. More preferably, during use of device 10, surfaces 62a, 62b should remain in the temperature range between and including about 75° C. to 100° C. Stated another way, surfaces 62a, 62b should be hot enough to shrink collagen in the range between and including about 1 second to 10 seconds after RF activation.

Figure 15:
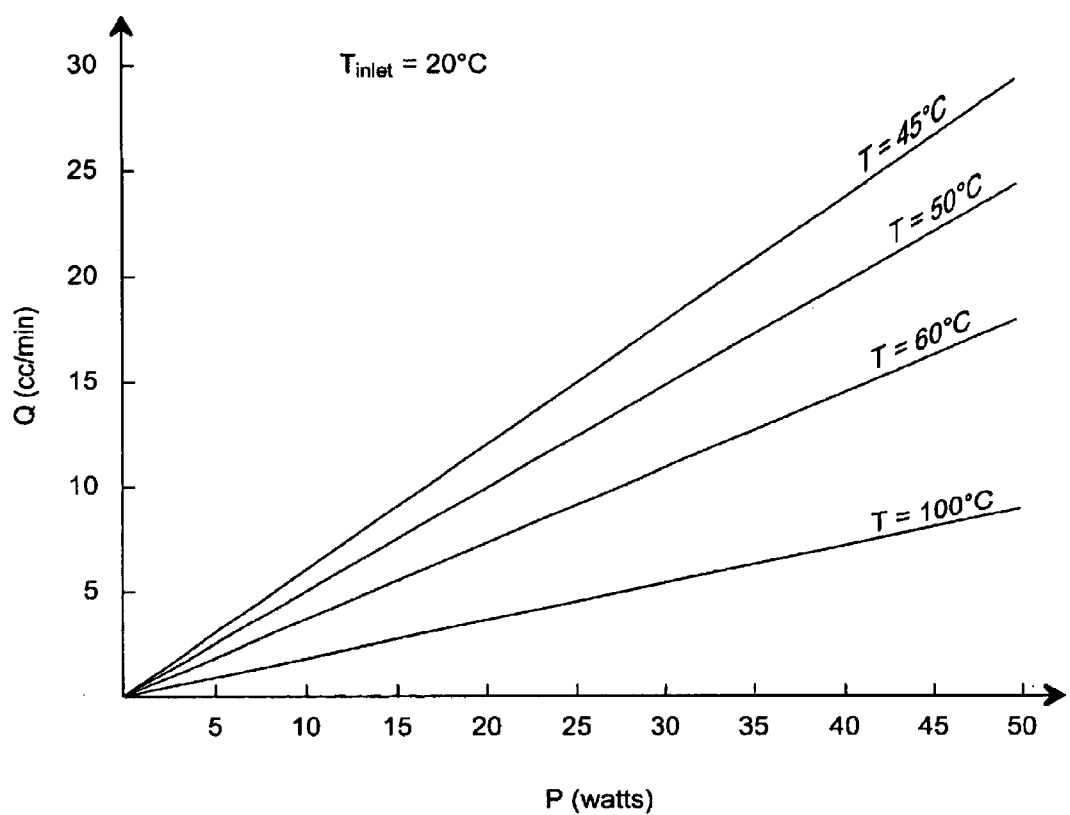
FIG. 15 is an exemplary graph that describes a relationship between RF power to tissue (P) versus flow rate of fluid (Q)

As shown in FIG. 11, RF power to tissue can vary even though the generator 136 has been "set" or "fixed" to a particular wattage. FIG. 15 shows an exemplary schematic graph that describes one relationship between the flow rate Q of fluid 128 (Y-axis in cc/min.) versus RF power P to tissue 156 (X-axis in watts). More precisely, as shown in FIG. 15, the relationship between the rate of fluid flow Q and RF power P may be expressed as a direct, linear relationship, when a steady-state condition has been achieved (temperature not changing with time).

Based on a simple, one-dimensional, steady-state, lumped parameter model of the heat transfer and a predetermined peak tissue temperature, the flow rate Q of fluid 128 corresponding to the peak tissue temperature can be determined. The RF electrical power P that is converted into heat can be defined as:

$$P = \rho_m c_\rho Q_1 \Delta T \tag{4}$$

where P=the RF electrical power that is converted into heat. The term $[\rho_m c_\rho Q_1 \Delta T]$ in equation (4) is heat used to warm up the flow of fluid 128 to peak temperature (without boiling the fluid), where:

$\rho_m$=Density of the fluid (approximately 1.0 gm/cm$^3$ for physiologic saline);

$c_\rho$=Specific heat of fluid (approximately 4.1 watt-sec/gm-° C. for physiologic saline);

$Q_1$=Flow rate of the fluid that is heated (cm$^3$/sec); and $\Delta T$=Temperature rise of the fluid. The difference in temperature between the peak fluid temperature and the initial (input) fluid temperature. The inlet fluid temperature is typically at ambient temperature or about 20° C. for a hospital operating room.

Assuming that the peak fluid temperature is the same as the peak tissue temperature at steady state, the flow rate for a predetermined peak fluid temperature (provided the temperature is at or below boiling of the fluid) can be determined by solving equation (4) for $Q_1$:

$$Q_1 = [P]/\rho_m c_\rho \Delta T \tag{5}$$

This equation defines the lines shown in FIG. 15 with a slope given by $1/(\rho_m c_\rho \Delta T)$. Assuming an inlet temperature of 20° C., FIG. 15 shows several lines for different outlet temperatures of 45, 50, 60 and 100° C.

Outside of surfaces 62a, 62b it is desirable to provide a tissue temperature which inhibits tissue necrosis. The onset of tissue necrosis will generally occur at about 60° C. with an exposure time of about 0.02 seconds. As temperature decreases, the time for tissue necrosis increases. For a tissue temperature of about 45° C., exposure time increases to about 15 minutes. Thus, an exemplary targeted steady state temperature is about 50° C.

Worse case, assuming all the power to tissue (i.e. here 35 watts) has to be removed by fluid 128 after the jaws 16a, 16b and fluid 128 have reached a targeted steady state temperature of 50° C., the calculated flow rate Q is [35]/(1)(4.1)(50−20)=0.28 cc/sec or about 17 cc/min.

It should be understood that the flow rate Q above is merely exemplary. An exemplary range of flow rates for device 10 is from about 0.01 cc/min. to about 100 cc/min.

In light of the above, an exemplary control strategy which can be employed for the device 10 is to provide a flow rate Q of fluid 128 to inhibit necrosis of tissue 156 outside surfaces 62a, 62b which may be subject to necrosis by the portion of the total power P provided to tissue 156 outside surfaces 62a, 62b.

In order to determine when a predetermined temperature of the fluid 128 has been achieved (e.g., when the fluid reaches, for example, 50° C.), a thermochromic material (a material that changes color as it is heated or cooled), such as a thermochromic dye (e.g., leuco dye), may be added to the fluid. The dye can be formulated to provide a first predetermined color to the fluid at temperatures below a predetermined temperature, such as 50° C., then, upon heating above 50° C., the dye provides a second color, such as clear, thus turning the fluid clear (i.e. no color or reduction in color). This color change may be gradual, incremental, or instant. Thus, a change in the color of the fluid, from a first color to a second color (or lack thereof) provides a visual indication to the user of the electrosurgical device 5 as to when a predetermined fluid temperature has been achieved. Thermochromic dyes are available, for example, from Color Change Corporation, 1740 Cortland Court, Unit A, Addison, Ill. 60101.

In some embodiments, it can be desirable to control the temperature of the fluid 128 before it is released from the device 10. In one embodiment, a heat exchanger is provided for the outgoing fluid flow to either heat or chill fluid 128. The heat exchanger may be provided as part of device 10 or as part of another part of the system, such as within the enclosure 152. Cooling the fluid 128 to a predetermined temperature, typically below room temperature, further inhibits thermal damage to tissue outside surfaces 62a, 62b. More specifically, the use of chilled saline (i.e. below room temperature of about 20° C. and of any salt concentration) will inhibit tissue damage outside surfaces 62a, 62b due to heat conduction. Flowing fluid 128 will absorb the heat from higher temperature tissue, dilute it with the cooler fluid 128 and remove it from the device 10. Chilling and convective cooling should not significantly affect the amount of resistance heating except by slightly increasing the electrical resistivity for saline and chilled tissue. Chilling and convective cooling with the fluid 128 will simply reduce the peak temperatures that are created in the tissue outside surfaces 62a, 62b.

In other embodiments, as shown in FIG. 16, electrodes 64a, 66a, 64b, 66b may be located at least partially directly beneath surfaces 62a, 62b. Consequently, with such a configuration, heat transfer from support members 58a, 58b and surfaces 62a, 62b may be further increased. As shown, support members 58a, 58b, particularly the portion underlying surfaces 62a, 62b, are convection cooled by flowing fluid 128 provided from side flow passages 92a, 94a, 92b, 94b of electrodes 64a, 66a, 64b, 66b. Furthermore, the support members 62a, 62b are also cooled via conduction of heat to the portions of electrodes 64a, 66a, 64b, 66b in direct contact therewith. This heat is then transferred via conduction through electrodes 64a, 66a, 64b, 66b to flowing fluid 124 contained within central fluid flow passage 84a, 86a, 84b, 86b where it is carried away through side flow passages 92a, 94a, 92b, 94b.

Preferably device 10 is provided with a means to inform the use of the device when tissue between surfaces 62a, 62b has been sufficiently coagulated. As known in the art, with the application of RF power through tissue its impedance changes. As shown by Bergdahl, the electrical impedance of tissue initially decreases (to an impedance value below its initial untreated impedance value) and then subsequently increases as the tissue desiccates and coagulates. (Bergdahl, J. Neurosurg., Vol. 75, July 1991, pages 148–151).

Correspondingly, in a constant voltage situation and by virtue of Ohm's law, the electrical current through the tissue initially increases (as tissue impedance decreases) and then decreases (as tissue impedance increases). Thus, the electrical current in the tissue is inversely proportional to the impedance.

However, prior art electrosurgical devices such as device 10 do not indicate the tissue impedance, or provide any visual or audible feedback as to the state of the tissue being treated at the targeted tissue treatment site. In a small number of instances, ammeters have been known to be located on generators, but due to relative location, for example in a hospital operating room, are not easily usable. Often the generator is removed from the patient and electrosurgical device, and not viewable by the user of the electrosurgical device without looking away from the surgical procedure. Consequently, clinical judgment and operator training are required to minimize or prevent incomplete coagulation or charring and sticking from overheating. If an under treated vessel is transected or cut, it may bleed or worse leak, often after the surgical incision is closed.

An advancement of the art would be to provide direct information when coagulation or other tissue treatment is completed, preferably such that the surgeon or other user of the electrosurgical device would be informed of the completion of tissue treatment while still looking towards the surgical procedure/patient and viewing the indicator within the their vision, either direct or indirect (peripheral) vision. Such would be particularly useful for laparoscopic surgery, particularly if the information was provided to the user of the device while viewing the peritoneal cavity.

As shown in FIGS. 1 and 9, in order for the operator or other user of device 10 to gauge the level of treatment for tissue 156 between surfaces 62a, 62b, device 10 may be provided with a tissue treatment indicator 184. Preferably the tissue treatment indicator 184 provides the user of device 10 with a visual output related to the level of treatment for tissue 156 between surfaces 62a, 62b. In one embodiment, the visual indicator preferably comprises a lighting device (e.g. incandescent bulb, halogen bulb, neon bulb). In another embodiment, the visual indicator preferably comprises a thermochromic device.

As shown in FIG. 9, for example, the present invention may use an incandescent bulb or thermochromic strip wired in parallel circuit configuration with a power feed line (e.g. wire conductor 40 of insulated wire 36 of cable 34) providing power to electrodes 64a, 66a, 64b, 66b of device 10 from generator 136. Consequently, the tissue treatment indicator 184, here comprising an incandescent bulb or thermochromic strip, may be provided with device 10 (as shown), the generator 136 or any of the wire connectors (e.g. cable 34) connecting device 10 and generator 136.

More specifically, as shown in FIG. 9, the incandescent bulb or thermochromic strip is preferably wired in parallel circuit with a short section of wire conductor 40 (e.g. between about 1 cm and 60 cm of insulated wire 36 of cable 34) within the confines of device 10 and mounted on device 10, such as on handle 22 or preferably the tip portion 14 (as shown in FIG. 1). Preferably the indicator 184 is mounted to the tip portion 14 of device 10 such that when the tip portion 14 is inserted into the peritoneal cavity, or other cavity, the indicator 184 is visible within the confines of the peritoneal cavity by a surgeon using a laproscopic viewing scope or camera as known in the art.

During use of device 10, the brightness and change in brightness of the indicator 184 during tissue coagulation can be used to indicate the level of coagulation and consequent coaptation of a vessel and tissue structure. More specifically, as the tissue impedance decreases initially, the indicator will increase in brightness (with increasing current) and thereafter decrease in brightness (with decreasing current) as the tissue impedance increases.

As shown in FIG. 11, the power P from generator 136 will remain constant as long as the impedance Z stays between a low impedance cut-off 168 and a high impedance cut-off 170. As indicated above, transformer 172 is configured to match the load impedance provided to generator 136 such that it is within the working range of the generator 136 and, more preferably in the working range between the low impedance cut-off 168 and high impedance cut-off 170.

Upon the application of device 10 to tissue, generally impedance will initially reside within the generator's working range between the low impedance cut-off 168 and high impedance cut-off 170. Before tissue is treated in any significant manner, the indicator 184 will provide a first brightness level which is representative of a first impedance level.

For a period thereafter, the tissue impedance decreases. From Ohm's law, the change in impedance (here decrease) over a constant power P output from generator 136 will result in a change in the current I (here increase) of the circuit. As the current increases, the brightness of the indicator 184 will correspondingly increase to a second brightness level which is representative of a second impedance level.

After reaching a minimum tissue impedance, the tissue impedance will change direction and begin to increase with tissue coagulation and desiccation. Here, the change in impedance (here increase) over a constant power P output from generator 136 will result in a change in the current I (here decrease) of the circuit. As the current decreases, the brightness of the indicator 184 will correspondingly decrease to a third brightness level which is representative of a third impedance level.

Thus from the above configuration, one would see current changes mirroring the tissue impedance changes. If the bulb (e.g. a tungsten filament type #47 or equivalent) were placed across a 1-foot segment of the power cable, the lamp brightness would provide visual indication of current. The lamp will glow brightly when device 10 is activated and the electrodes are in good contact with the tissue. Subsequently, there will be a marked decrease in brightness or dimming of the lighted bulb as coagulation advances and is completed.

The jaw configurations described above may be particularly useful for use through a 12 mm or greater diameter trocar cannula. In still other embodiments, the jaws may be configured to use through a 3 mm, 5 mm, 10 mm or greater diameter trocar cannula. As shown in FIG. 17, in order to reduce size and complexity, the two electrodes from jaw 16a have been eliminated (i.e. 64a, 66a). Furthermore, as shown, preferably the two remaining electrodes, here 64b, 66b, are located on the same jaw 16b. Furthermore, the cutting mechanism 32 and the base 60a have also been eliminated. Also as shown, jaw 16a is configured substantially asymmetrical to jaw 16b and has a much flatter profile. In this manner, jaws 16a, 16b may function as tissue dissectors. In other words, while jaws 16a, 16b are in the closed position and without tissue there between, they are wedged into tissue, preferably between adjacent tissue planes. Thereafter, the jaws 16a, 16b may be slowly opened and, due to the separation forces placed on the tissue at the distal end 56 of the jaws 16a, 16b, the tissue will dissect.

FIGS. 18–21 show another embodiment of the present invention with the medial portion of the backside surfaces 120a, 120b of jaws 16a, 16b comprising a substantially flat surface as opposed to the arcuate surface of previous embodiments.

Figure 22:
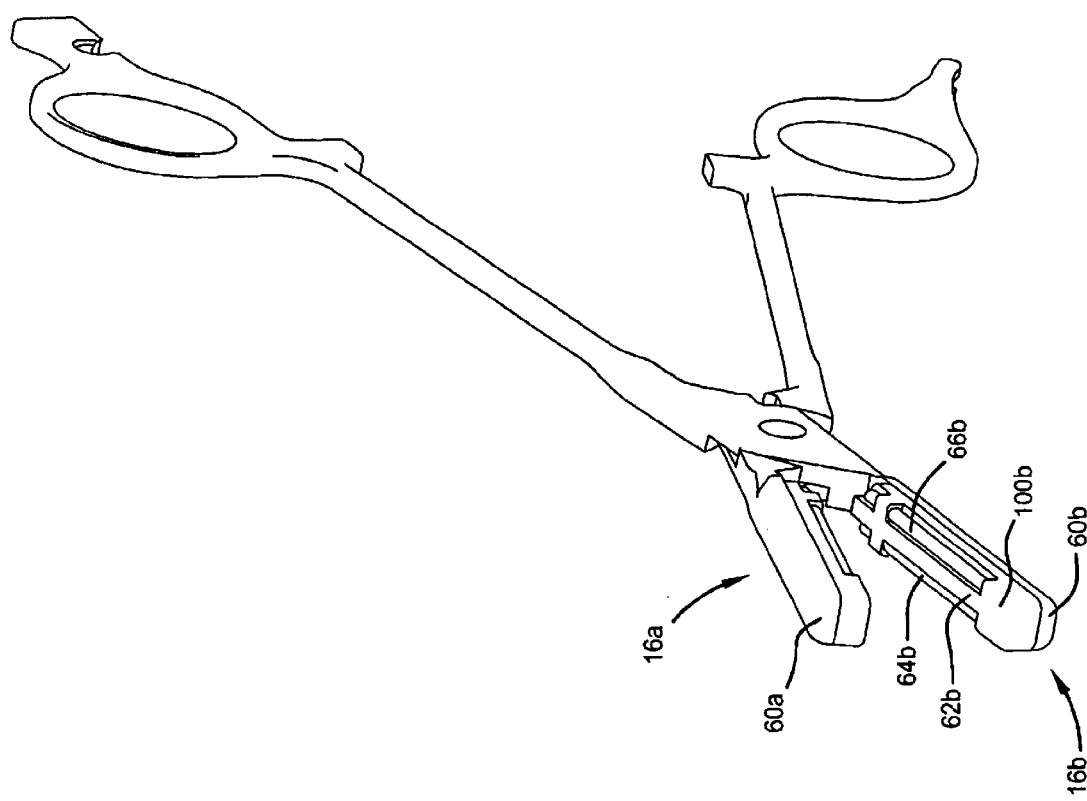
FIG. 22 is an isometric view of another exemplary device according to the present invention.

Thus far the device 10 has been described relative to use with an endoscopic grasper, and in particular endoscopic forceps. In still other embodiments, as shown in FIG. 22, the present tissue grasper of the present invention may comprise an open surgery grasper and more particularly open surgery forceps.

For purposes of the appended claims, the term "tissue" includes, but is not limited to, organs (e.g. liver, lung, spleen, gallbladder), highly vascular tissues (e.g. liver, spleen), soft and hard tissues (e.g. adipose, areolar, bone, bronchus-associated lymphoid, cancellous, chondroid, chordal, chromaffin, cicatricial, connective, elastic, embryonic, endothelial, epithelial, erectile, fatty, fibrous, gelatiginous, glandular, granulation, homologous, indifferent, interstitial, lymphadenoid, lymphoid, mesenchymal, mucosa-associated lymphoid, mucous, muscular, myeloid, nerve, osseous, reticular, scar, sclerous, skeletal, splenic, subcutaneous) and tissue masses (e.g. tumors).

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes, to the extent they are consistent.

What is claimed:

1. A tissue grasping device comprising:

a tip portion including a first jaw and a second jaw, at least one of the jaws being movable toward the other jaw;

the first jaw including a first jaw tissue grasping surface and the second jaw including a second jaw tissue grasping surface, the tissue grasping surface of each jaw comprising an electrically insulative surface;

a bipolar electrode configuration comprising first and second electrodes configured to be connected to a radio frequency generator to generate an electrical current therebetween, the first electrode having a first electrode surface and the second electrode having a second electrode surface;

at least one fluid passage configured to be connected to a fluid source;

at least one fluid outlet in fluid communication with the fluid passage, the at least one fluid outlet to expel a fluid from the fluid source;

the first electrode located on a left-side portion of either the first jaw or the second jaw, the first electrode surface separated from the tissue grasping surface of the jaw on which the first electrode is located by a left-side gap for fluid; and the second electrode located on a right-side portion of either the first jaw or the second jaw, the second electrode surface separated from the tissue grasping surface of the jaw on which the second electrode is located by a right-side gap for fluid.

2. The tissue grasping device of claim 1 wherein:

the tip portion is configured to provide radio frequency power from the radio frequency generator simultaneously with the fluid from the fluid source to treat tissue, the radio frequency power provided from the electrodes and the fluid provided from the at least one fluid outlet.

3. The tissue grasping device of claim 2 wherein:

the tip portion is further configured to provide the radio frequency power at least partially through at least one fluid coupling connecting one of the electrodes to a portion of the tissue, the at least one fluid coupling comprising the fluid from the fluid source.

4. The tissue grasping device of claim 1:

the first and second electrodes are configured to treat tissue with radio frequency power from the radio frequency generator in the presence of first and second fluid couplings connecting the first and second electrodes to first and second portions of tissue, respectively;

the first fluid coupling comprising a first portion of the fluid from the fluid source and at least partially located in the left-side gap; and the second fluid coupling comprising a second portion of the fluid from the fluid source and at least partially located in the right-side gap.

5. The tissue grasping device of claim 1 wherein:

the left-side gap is to provide a location for at least a portion of a left-side fluid coupling connecting the first electrode to a first portion of tissue; and the right-side gap is to provide a location for at least a portion of a right-side fluid coupling connecting the second electrode to a second portion of tissue.

6. The tissue grasping device of claim 1 wherein:

the tissue grasping surface of at least one jaw comprises a hydrophobic surface.

7. The tissue grasping device of claim 1 wherein:

the tissue grasping surface of at least one jaw comprises a textured surface.

8. The tissue grasping device of claim 1 wherein:

the tissue grasping surface of at least one jaw comprises a surface roughness between about 10 and 500 microns.

9. The tissue grasping device of claim 1 wherein:

the tissue grasping surface of at least one jaw comprises one or more serrations.

10. The tissue grasping device of claim 1 wherein:

the tissue grasping surface of at least one jaw has a contact angle ($\theta$) with the fluid from the fluid source when located thereon equal to or greater than about 30 degrees.

11. The tissue grasping device of claim 1 wherein:

the tissue grasping surface of at least one jaw is at least partially defined by a beveled edge.

12. The tissue grasping device of claim 1 wherein:

the tissue grasping surface of at least one jaw comprises a material with a thermal conductivity at 300° K (Kelvin) equal or greater than about 0.01 watt/cm° K.

13. The tissue grasping device of claim 1 wherein:

the tissue grasping surface of at least one jaw is supported by a support structure; and the tissue grasping surface of the at least one jaw is provided at least partially by a coating overlying the support structure.

14. The tissue grasping device of claim 1 wherein:

the tissue grasping surface of at least one jaw further comprises a medial portion, the medial portion supported therebeneath by a support structure comprising a material with a thermal conductivity at 300° K (Kelvin) equal or greater than about 0.01 watt/cm° K.

15. The tissue grasping device of claim 1 wherein:

the tissue grasping surface of at least one jaw further comprises a medial portion, the medial portion supported therebeneath by a support structure which provides a heat sink for transferring heat away from the tissue grasping surface.

16. The tissue grasping device of claim 1 wherein:

the at least one fluid outlet in fluid communication with the fluid passage further comprises a first fluid outlet and a second fluid outlet;

the first fluid outlet being located on the same jaw as the first electrode; and the second fluid outlet being located on the same jaw as the second electrode.

17. The tissue grasping device of claim 16 wherein:

the first fluid outlet and the second fluid outlet are configured to provide the fluid from the fluid source to tissue located outside of the tissue grasping surfaces.

18. The tissue grasping device of claim 16 wherein:

the first fluid outlet and the second fluid outlet are configured to provide the fluid from the fluid source to tissue located outside of and adjacent the tissue grasping surfaces.

19. The tissue grasping device of claim 16 wherein:

the first fluid outlet and the second fluid outlet are configured to provide the fluid from the fluid source to tissue located outside of and separated from the tissue grasping surfaces.

20. The tissue grasping device of claim 16 wherein:

the first fluid outlet is configured to provide a first portion of the fluid from the fluid source to tissue located adjacent the first electrode surface; and the second fluid outlet is configured to provide a second portion of the fluid from the fluid source to tissue located adjacent the second electrode surface.

21. The tissue grasping device of claim 16 wherein:

the first fluid outlet is configured to provide a first portion of the fluid from the fluid source between the first electrode surface and a first portion of tissue; and the second fluid outlet is configured to provide a second portion of the fluid from the fluid source between the second electrode surface and a second portion of tissue.

22. The tissue grasping device of claim 16 wherein:

the first fluid outlet is configured to provide a first portion of the fluid from the fluid source between the first electrode surface and the tissue grasping surface of the jaw on which the first electrode is located; and the second fluid outlet is configured to provide a second portion of the fluid from the fluid source between the second electrode surface and the tissue grasping surface of the jaw on which the second electrode is located.

23. The tissue grasping device of claim 16 wherein:

the first fluid outlet is configured to provide a first portion of the fluid from the fluid source to the first electrode surface; and the second fluid outlet is configured to provide a second portion of the fluid from the fluid source to the second electrode surface.

24. The tissue grasping device of claim 16 wherein:

the first fluid outlet is configured to provide a first portion of the fluid from the fluid source to a first portion of one or the other of the jaws outside the tissue grasping surface; and the second fluid outlet is configured to provide a second portion of the fluid from the fluid source to a second portion of one or the other of the jaws outside the tissue grasping surface.

25. The tissue grasping device of claim 1 wherein:

the at least one fluid outlet in fluid communication with the fluid passage further comprises a first plurality of fluid outlets and a second plurality of fluid outlets, the first plurality of fluid outlets being located on the same jaw as the first electrode and the second plurality of fluids outlet being located on the same jaw as the second electrode.

26. The tissue grasping device of claim 1 wherein:

the first electrode surface is configured for a first portion of the fluid from the fluid source to form a film at least partially thereon; and the second electrode surface is configured for a second portion of the fluid from the fluid source to form a film at least partially thereon.

27. The tissue grasping device of claim 1 wherein:

the at least one fluid passage further comprises a first fluid passage and a second fluid passage;

the first fluid passage being located on the same jaw as the first electrode; and the second fluid passage being located on the same jaw as the second electrode.

28. The tissue grasping device of claim 27 wherein:

the first electrode defines at least a portion of the first fluid passage; and the second electrode defines at least a portion of the second fluid passage.

29. The tissue grasping device of claim 27 wherein:

the first electrode and the second electrode are each provided by an elongated structure having a cavity therein;

the first fluid passage at least partially defined by the cavity of the first electrode structure; and the second fluid passage at least partially defined by the cavity of the second electrode structure.

30. The tissue grasping device of claim 29 wherein:

the first electrode and the second electrode each comprise metal tubing.

31. The tissue grasping device of claim 1 wherein:

at least a portion of each gap is configured to receive a portion of the fluid expelled from the fluid outlet therein.

32. The tissue grasping device of claim 31 wherein:

the portion of each gap configured to receive a portion of the fluid expelled from the fluid outlet therein is positioned for the fluid therein to remove heat generated during use of the device from at least one of tissue and the device.

33. The tissue grasping device of claim 31 wherein:

the fluid from the fluid source comprises an electrically conductive fluid; and the portion of each gap configured to receive a portion of the fluid expelled from the fluid outlet therein is positioned for the fluid therein to provide an electrical path for an electrical current.

34. The tissue grasping device of claim 33 wherein:
the portion of each gap configured to receive a portion of the fluid from the fluid outlet expelled from the fluid outlet therein is further positioned for the fluid therein to provide an electrical path outside the tissue grasping surfaces, whereby the heating of tissue located outside the tissue grasping surfaces may be reduced.

35. The tissue grasping device of claim 1 wherein:
each gap further comprises an elongated gap.

36. The tissue grasping device of claim 35 wherein:
each elongated gap is configured to provide a fluid trough.

37. The tissue grasping device of claim 1 wherein:
at least one jaw comprises at least one stand-off configured to keep tissue from physically contacting at least one of the first electrode surface and the second electrode surface.

38. The tissue grasping device of claim 1 further comprising:
at least one jaw further comprises at least one obstruction configured to inhibit a fluid shunt from forming between the first electrode and the second electrode.

39. The tissue grasping device of claim 1 further comprising:
a tissue treatment indicator which provides an output related to the level of treatment of tissue.

40. The tissue grasping device of claim 39 wherein:
the tissue treatment indicator is located on the tip portion.

41. A tissue grasping device comprising:
a tip portion including a first jaw and a second jaw, at least one of the jaws being movable toward the other jaw;
each jaw including a tissue grasping surface, the tissue grasping surface of each jaw further comprising an electrically insulative surface;
a portion of each tissue grasping surface being located on each side of a center plane, the center plane orientated longitudinal and perpendicular to the tissue grasping surface;
a bipolar electrode configuration comprising first and second electrodes configured to be connected to a radio frequency generator to generate an electrical current therebetween, the first electrode having a first electrode surface and the second electrode having a second electrode surface;
at least one fluid passage configured to be connected to a fluid source;
at least one fluid outlet in fluid communication with the fluid passage, the at least one fluid outlet to expel a fluid from the fluid source;
one of the first and second electrodes being located on one or the other of the jaws on one side of the center plane and the other of the electrodes being located on one or the other of the jaws on the other side of the center plane; and
each of the first and second electrode surfaces being separated from the tissue grasping surface of the jaw to which it is located by first and second gaps for fluid, respectively.

42. The tissue grasping device of claim 41 wherein:
the tissue grasping surface of at least one jaw has a contact angle (θ) with the fluid from the fluid source when located thereon equal to or greater than about 30 degrees.

43. The tissue grasping device of claim 41 wherein:
the at least one fluid outlet in fluid communication with the fluid passage further comprises a first fluid outlet and a second fluid outlet;

the first fluid outlet being located on the same jaw as the first electrode; and
the second fluid outlet being located on the same jaw as the second electrode.

44. The tissue grasping device of claim 43 wherein:
the first fluid outlet is configured to provide a first portion of the fluid from the fluid source between the first electrode surface and a first portion of tissue; and
the second fluid outlet is configured to provide a second portion of the fluid from the fluid source between the second electrode surface and a second portion of tissue.

45. The tissue grasping device of claim 41 wherein:
at least a portion of each gap is configured to receive a portion of the fluid expelled from the fluid outlet therein.

46. The tissue grasping device of claim 45 wherein:
the portion of each gap configured to receive a portion of the fluid expelled from the fluid outlet therein is positioned for the fluid therein to remove heat generated during use of the device from at least one of tissue and the device.

47. The tissue grasping device of claim 45 wherein:
the fluid from the fluid source comprises an electrically conductive fluid; and
the portion of each gap configured to receive a portion of the fluid expelled from the fluid outlet therein is positioned for the fluid therein to provide an electrical path for an electrical current.

48. The tissue grasping device of claim 41 wherein:
each gap further comprises an elongated gap.

49. The tissue grasping device of claim 41 further comprising:
at least one jaw further comprises at least one obstruction configured to inhibit a fluid shunt from forming between the first electrode and the second electrode.

50. A tissue grasping device comprising:
a tip portion including a first jaw and a second jaw, at least one of the jaws being movable toward the other jaw;
each jaw including a tissue grasping surface, the tissue grasping surface of each jaw further comprising an electrically insulative surface;
a portion of each tissue grasping surface being located on two opposing sides of a cutting mechanism, the cutting mechanism comprising a blade;
a bipolar electrode configuration comprising first and second electrodes configured to be connected to a radio frequency generator to generate an electrical current therebetween, the first electrode having a first electrode surface and the second electrode having a second electrode surface;
at least one fluid passage configured to be connected to a fluid source;
at least one fluid outlet in fluid communication with the fluid passage, the at least one fluid outlet to expel a fluid from the fluid source;
one of the first and second electrodes being located on one or the other of the jaws on one side of the cutting mechanism and the other of the electrodes being located on one or the other of the jaws on the other side of the cutting mechanism; and
each the first and second electrode surfaces being separated from the tissue grasping surface of the jaw to which it is located by first and second gaps for fluid, respectively.

51. The tissue grasping device of claim 50 wherein:

the tissue grasping surface of at least one jaw has a contact angle (θ) with the fluid from the fluid source when located thereon equal to or greater than about 30 degrees.

52. The tissue grasping device of claim 50 wherein:

the at least one fluid outlet in fluid communication with the fluid passage further comprises a first fluid outlet and a second fluid outlet;

the first fluid outlet being located on the same jaw as the first electrode; and the second fluid outlet being located on the same jaw as the second electrode.

53. The tissue grasping device of claim 52 wherein:

the first fluid outlet is configured to provide a first portion of the fluid from the fluid source between the first electrode surface and a first portion of tissue; and the second fluid outlet is configured to provide a second portion of the fluid from the fluid source between the second electrode surface and a second portion of tissue.

54. The tissue grasping device of claim 50 wherein:

at least a portion of each gap is configured to receive a portion of the fluid expelled from the fluid outlet therein.

55. The tissue grasping device of claim 54 wherein:

the portion of each gap configured to receive a portion of the fluid expelled from the fluid outlet therein is positioned for the fluid therein to remove heat generated during use of the device from at least one of tissue and the device.

56. The tissue grasping device of claim 54 wherein:

the fluid from the fluid source comprises an electrically conductive fluid; and the portion of each gap configured to receive a portion of the fluid expelled from the fluid outlet therein is positioned for the fluid therein to provide an electrical path for an electrical current.

57. The tissue grasping device of claim 50 wherein:

each gap further comprises an elongated gap.

58. The tissue grasping device of claim 50 further comprising:

at least one jaw further comprises at least one obstruction configured to inhibit a fluid shunt from forming between the first electrode and the second electrode.

* * * * *